(12) United States Patent
Tierney et al.

(10) Patent No.: US 8,318,048 B2
(45) Date of Patent: Nov. 27, 2012

(54) PROCESS FOR PREPARING SUBSTITUTED PENTACENES

(75) Inventors: Steven Tierney, Southampton (GB); Martin Heeney, Southampton (GB); Clare Bailey, Southampton (GB); Weimin Zhang, Southampton (GB)

(73) Assignee: Merck Patent GmbH, Darmstadt (DE)

( * ) Notice: Subject to any disclaimer, the term of this patent is extended or adjusted under 35 U.S.C. 154(b) by 442 days.

(21) Appl. No.: 12/596,198

(22) PCT Filed: Mar. 28, 2008

(86) PCT No.: PCT/EP2008/002485
§ 371 (c)(1),
(2), (4) Date: Oct. 16, 2009

(87) PCT Pub. No.: WO2008/128618
PCT Pub. Date: Oct. 30, 2008

(65) Prior Publication Data
US 2010/0127220 A1    May 27, 2010

(30) Foreign Application Priority Data
Apr. 19, 2007 (EP) .................... 07007947

(51) Int. Cl.
*H01B 1/00* (2006.01)
*H01B 1/12* (2006.01)
*C09K 11/06* (2006.01)
*C07C 45/27* (2006.01)
*C07C 50/18* (2006.01)

(52) U.S. Cl. .............. 252/500; 252/301.16; 257/40; 552/208; 556/431; 568/58; 568/632; 585/26

(58) Field of Classification Search .................. 252/500, 252/301.16; 257/40; 552/208; 556/431; 568/632, 633, 634, 58; 570/183; 585/26
See application file for complete search history.

(56) References Cited

FOREIGN PATENT DOCUMENTS
WO    WO 2005/055248 A2 *   6/2005
WO    PCTEP2008002485 R    6/2008

OTHER PUBLICATIONS

Christopher R. Swartz, Sean R. Parkin,Joseph E. Bullock, John E. Anthony, Alex C. Mayer, and George G. Malliaras, Synthesis and Characterization of Electron-Deficient Pentacenes, Org. Lett., vol. 7, No. 15, 2005,© 2005 American Chemical Society.*

Swartz, Christopher R. et al. "Synthesis and Characterization of Electron-Deficient Pentacenes." (Organic Letters), Jun. 30, 2005, 3163-3166, 7:15.

* cited by examiner

*Primary Examiner* — Bijan Ahvazi
(74) *Attorney, Agent, or Firm* — Millen, White, Zelano & Branigan, P.C.

(57) ABSTRACT

The invention relates to a process of preparing substituted pentacenes, to novel pentacenes prepared by this process, to the use of the novel pentacenes as semiconductors or charge transport materials in optical, electrooptical or electronic devices including field effect transistors (FETs), electroluminescent, photovoltaic and sensor devices, and to FETs and other semiconducting components or materials comprising the novel pentacenes.

16 Claims, 5 Drawing Sheets

PROCESS FOR PREPARING SUBSTITUTED PENTACENES

FIELD OF INVENTION

The invention relates to a process for preparing substituted pentacenes, and to novel pentacenes prepared by this process. The invention further relates to the use of the novel pentacenes as semiconductors or charge transport materials in optical, electrooptical or electronic devices including field effect transistors (FETs), electroluminescent, photovoltaic and sensor devices. The invention further relates to FETs and other semiconducting components or materials comprising the novel pentacenes.

BACKGROUND AND PRIOR ART

In recent years, there has been development of organic semiconducting materials in order to produce more versatile, lower cost electronic devices. Such materials find application in a wide range of devices or apparatus, including organic field effect transistors (OFETs), organic light emitting diodes (OLEDs), photodetectors, photovoltaic (PV) cells, sensors, memory elements and logic circuits to name just a few. The organic semiconducting materials are typically present in the electronic device in the form of a thin layer, for example less than 1 micron thick.

Pentacene has shown promise as an organic semiconducting material. Pentacene has been described as requiring a highly crystalline structure in order to provide a molecular orientation which results in good charge mobility. Thus, in the prior art, thin films of pentacene have been vapour deposited, due in part to the fact that pentacene is rather insoluble in common solvents. However, vapour deposition requires expensive and sophisticated equipment. In view of the latter problem, one approach has been to apply a solution containing a precursor pentacene and then chemically converting, for example by heat, the precursor compound into pentacene. However, the latter method is also complex and it is difficult to control in order to obtain the necessary ordered structure for good charge mobility.

Soluble pentacene compounds comprising silylethynyl groups, like 6,13-bis(triethylsilylethynyl)pentacene have recently been described in the prior art as organic semiconducting compounds [1,2]. This compound exhibits high performance as the semiconducting layer in an organic field-effect transistor (OFET), with mobility of 0.4 $cm^2/Vs$ and current on/off ratio of $10^6$ measured [3]. Meanwhile, significant work has been undertaken by various groups to design and prepare soluble pentacene materials that offer even higher performance in terms of semiconducting properties, and that also show enhanced processability and environmental stability.

However, the properties of the bis(silylethynyl)pentacenes described in prior art still leave room for further improvement. For example, pentacene type molecules degrade in the presence of air and light due to a photooxidation process [21,22].

One aim of the present invention was to provide further pentacene compounds that are useful as organic semiconducting materials.

In prior art 6,13-bis(trialkylsilylethynyl)pentacenes with additional substituents in 1-, 2-, 3-, 8-, 9-, 10- and/or 11-position are disclosed [23].

By adding substituents in these positions, which are prone to the above-described photo-oxidation process, it is possible to hinder the degradation. This leads to polyacenes that are useful as charge transport and semiconducting materials and have improved solubility and charge carrier mobility and improved stability especially against air, heat and light. Furthermore, when these substituted polyacenes are provided in a formulation together with an organic binder, improved semiconducting materials with good processibility are obtained which do still show a surprisingly high charge carrier mobility.

The inventors of the present invention have now found that especially pentacenes with substituents in 1-, 4-, 8- and 11-position do unexpectedly show high charge carrier mobility, good solubility in standard organic solvents, and good processibility.

However, it was also found that such substituted pentacenes are difficult to synthesize. Generally, pentacene ring-network precursors have previously been constructed using either the Aldol condensation [4] or the Cava reaction [5]. However, the inventors have found that for 1,4,8,11-tetrasubstituted 6,13-bis(triethylsilylethynyl) pentacene both the Aldol and Cava methodologies yield little success in constructing the pentacene ring-network precursors in high and reproducible yields. Therefore a more successful alternative method is high desirable.

Thus, another aim of the present invention was to find an improved synthesis method for 1,4,8,11-substituted pentacenes. Other aims of the present invention are immediately evident to the expert from the following detailed description.

It was now found that these aims can be achieved by providing methods and materials as claimed in the present invention. In particular, this invention relates to a new synthetic route to prepare 1,4,8,11-tetrasubstituted pentacene, which circumvents the key drawbacks of the previous routes based around the Aldol condensation or the Cava reaction. Furthermore, it provides novel 1,4,8,11-tetrasubstituted pentacenes with improved properties, especially high charge carrier mobility, high solubility and good processibility.

SUMMARY OF THE INVENTION

The invention relates to a process for preparing a 1,4,8,11-tetrasubstituted pentacene comprising the following steps a1) reduction of a 4,7-disubstituted isobenzofuran-1,3-dione (2) in the presence of a reducing agent to form the 4,7-disubstituted 3H-isobenzofuran-1-one (4), or a2) oxidation of a 1,2-bis(hydroxymethyl)-3,6-disubstituted benzene (3) in the presence of an oxidizing agent to form a 4,7-disubstituted 3H-isobenzofuran-1-one (4), or a3) oxidation of a 1,2-bis(hydroxymethyl)-3,6-disubstituted benzene (3) in the presence of an oxidizing agent to form a 4,7-disubstituted 1-hydroxy-1,3-dihydro-isobenzofuran (5a), and, in case of step a1) or step a2), b) reduction of the product (4) of step a1) or a2) in the presence of a reducing agent to form a 4,7-disubstituted 1-hydroxy-1,3-dihydro-isobenzofuran (5a), and c) methylation of the product (5a) of step a3) or b) to form a 4,7-disubstituted 1-methoxy-1,3-dihydro-isobenzofuran (5b), d) elimination of the product (5b) of step c) in the presence of a base to form a 4,7-disubstituted isobenzofuran (6), e) reacting the product (6) of step d) with p-benzoquinone by Diels-Alder cycloaddition to form a bis-cycloadduct (7), f) dehydration of the product (7) of step e) in the presence of a base to form a 1,4,8,11-tetrasubstituted 6,13-pentacene-quinone (8), g) alkynation of the product (8) of step f) with a monosubstituted metal acetylide to form a 1,4,8,11-tetrasubstituted 6,13-bis(1-substituted ethynyl)pentacene (9).

The invention further relates to novel substituted pentacenes, in particular novel 1,4,8,11-tetrasubstituted 6,13-bis(1-substituted ethynyl) pentacenes, obtainable or obtained by a process as described above and below.

The invention further relates to a semiconductor or charge transport material, component or device comprising one or more substituted pentacenes as described above and below.

The invention further relates to a formulation comprising one or more compounds according to the present invention and one or more solvents, preferably selected from organic solvents.

The invention further relates to an organic semiconducting formulation comprising one or more compounds of formula I, one or more organic binders, or precursors thereof, preferably having a permittivity $\in$ at 1,000 Hz of 3.3 or less, and optionally one or more solvents.

The invention further relates to the use of compounds and formulations according to the present invention as charge transport, semiconducting, electrically conducting, photoconducting or light emitting material in an optical, electrooptical, electronic, electroluminescent or photoluminescent components or devices.

The invention further relates to a charge transport, semiconducting, electrically conducting, photoconducting or light emitting material or component comprising one or more compounds or formulations according to the present invention.

The invention further relates to an optical, electrooptical, electronic, electroluminescent or photoluminescent component or device comprising one or more compounds or formulations according to the present invention.

Said components and devices include, without limitation, electrooptical displays, LCDs, optical films, retarders, compensators, polarisers, beam splitters, reflective films, alignment layers, colour filters, holographic elements, hot stamping foils, coloured images, decorative or security markings, LC pigments, adhesives, non-linear optic (NLO) devices, optical information storage devices, electronic devices, organic semiconductors, organic field effect transistors (OFET), integrated circuits (IC), thin film transistors (TFT), Radio Frequency Identification (RFID) tags, organic light emitting diodes (OLED), organic light emitting transistors (OLET), electroluminescent displays, organic photovoltaic (OPV) devices, organic solar cells (O-SC), organic laser diodes (O-laser), organic integrated circuits (O-IC), lighting devices, sensor devices, electrode materials, photoconductors, photodetectors, electrophotographic recording devices, capacitors, charge injection layers, Schottky diodes, planarising layers, antistatic films, conducting substrates, conducting patterns, photoconductors, electrophotographic applications, electrophotographic recording, organic memory devices, biosensors, biochips.

DETAILED DESCRIPTION OF THE INVENTION

This invention relates to a new synthetic route to prepare 1,4,8,11-tetrasubstituted pentacene whereby the pentacene ring-network precursor is constructed using a Diels-Alder cycloaddition reaction involving an isobenzofuran intermediate. The invention further relates to novel substituted pentacenes with improved properties.

One preferred compound that exhibits improved semiconducting properties is 1,4,8,11-tetramethyl-6,13-bis(triethylsilylethynyl)pentacene. When using this compound in the semiconducting layer of an OFET device, a mobility of 6 $cm^2/Vs$ is measured.

Each of the synthetic routes for preparing substituted pentacenes according to prior art, which are based around the Aldol condensation or the Cava reaction, has certain drawbacks.

Figure 1:
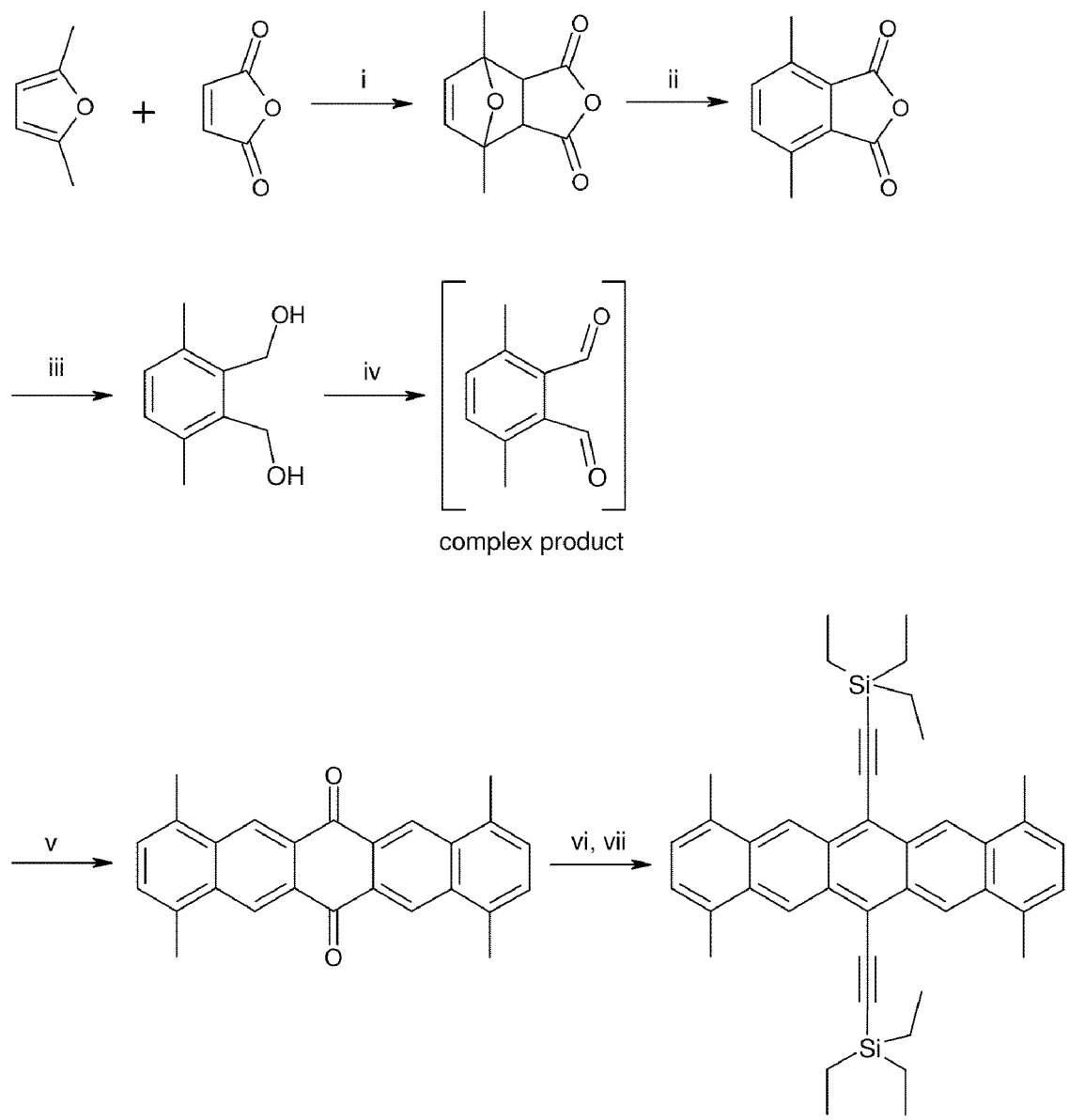
FIG. 1 shows the Aldol route for the preparation of tetrasubstituted pentacenes.

For example, FIG. 1 exemplarily shows the Aldol route known from prior art, which has here been adapted to the synthesis of 1,4,8,11-tetramethyl-6,13-bis(triethylsilylethynyl)pentacene.

The reagents used for the process steps of FIG. 1 are as follows: i. $Et_2O$; ii. conc. $H_2SO_4$; iii. $LiAlH_4$, THF; iv. DMSO, $(COCl)_2$, $Et_3N$, DCM; v. 1,4-cyclohexadione, 5% KOH, IMS; vi. triethylsilyl-acetylene, n-BuLi, $Et_2O$, THF; vii. $SnCl_2$, 10% HCl.

In this method, the problem is that isolation of the dicarboxyaldehyde intermediate, like e.g. 3,6-dimethylbenzene-1,2-bis(carboxyaldehyde), is not possible. A variety of oxidation methods to obtain the dicarboxyaldehyde intermediate from the diol, 3,6-dimethylbenzene-1,2-bis(methanol), have been tested. Some oxidation methods (using manganese(IV) oxide or pyridinium chlorochromate) result in the formation of the lactone product, 4,7-dimethyl-3H-isobenzofuran-1-one, which cannot be further reacted in the Aldol condensation step. Whereas the Swern oxidation (using dimethyl sulfoxide/oxalyl chloride) yields a complex product that cannot be clearly identified by proton NMR spectroscopy. This complex product when reacted in the Aldol condensation step does however yield the pentacenequinone product, and so the dicarboxyaldehyde must have been regenerated from this complex product under these conditions. However, the yield is low and the reaction suffers from poor reproducibility.

Figure 2:
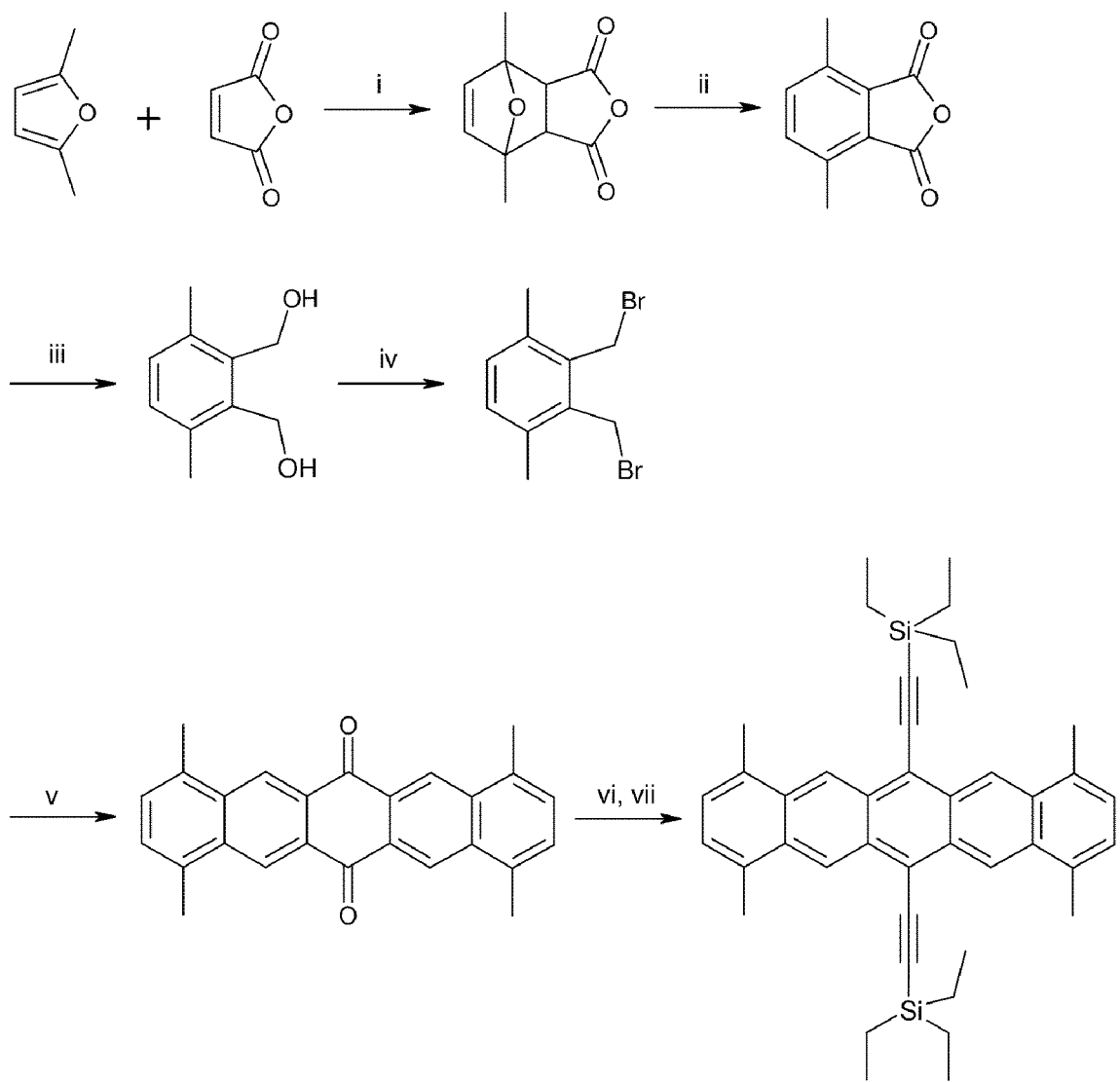
FIG. 2 shows the Cava route for the preparation of tetrasubstituted pentacenes.

FIG. 2 exemplarily shows the Cava route known from prior art, which has here been adapted to the synthesis of 1,4,8,11-tetramethyl-6,13-bis(triethylsilylethynyl)pentacene.

The reagents used for the process steps of FIG. 2 are as follows: i. $Et_2O$; ii. conc. $H_2SO_4$; iii. $LiAlH_4$, THF; iv. $PBr_3$, $Et_2O$; v. p-benzoquinone, KI, DMF; vi. triethylsilyl-acetylene, n-BuLi, $Et_2O$, THF; vii. $SnCl_2$, 10% HCl.

Here, the problem is that reaction between the bis(bromomethyl) intermediate and p-benzoquinone to form the pentacenequinone product gives very low yields.

The inventors of the present invention have found an alternative route to 1,4,8,11-tetrasubstituted pentacene. In the literature there is an isolated report of the synthesis of pentacenequinone via a Diels-Alder reaction between isobenzofuran and p-benzoquinone under acidic conditions [6]. Therefore, it was envisaged that by preparing the appropriate isobenzofuran derivative and reacting it with p-benzoquinone, the pentacenequinone product can be prepared. However, the required 4,7-disubstituted isobenzofuran derivatives (like 4,7-dimethyl-isobenzofuran) have not been previously prepared, nor has their reaction with p-benzoquinone been reported.

Figure 3:
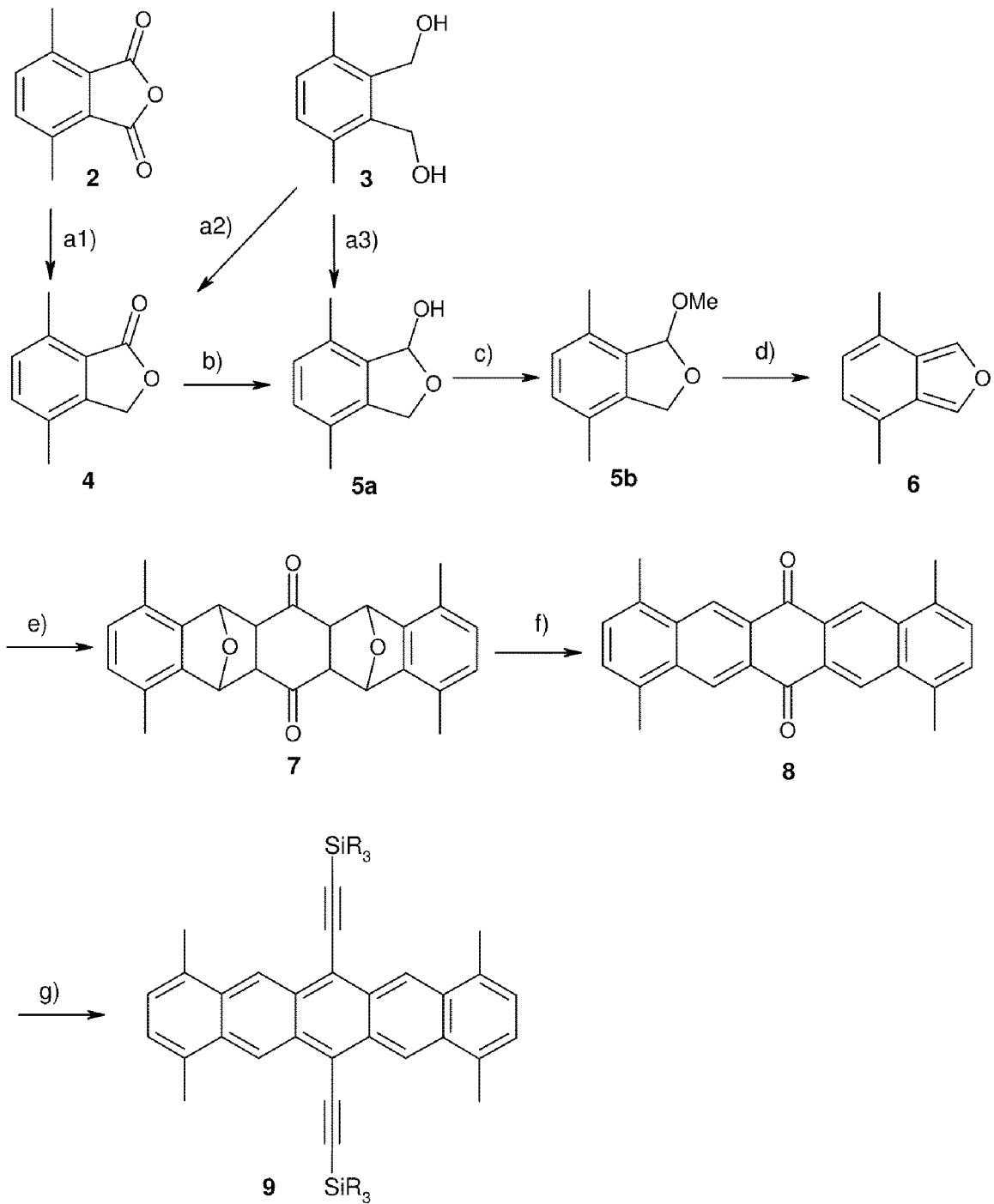
FIG. 3 exemplarily shows the process according to the present invention for the preparation of tetrasubstituted pentacenes.

A preferred process of the present invention is exemplarily illustrated in FIG. 3 for the preparation of 1,4,8,11-tetramethyl-6,13-bis(trialkylsilyl-ethynyl) pentacene 9. The reagents used in the process steps shown in FIG. 3 are as follows: a1) $NaBH_4$, THF or Zn, HOAc; a2) $MnO_2$, DCM; a3) 2-iodoxybenzoic acid (IBX); b) DiBAL, toluene, $Et_2O$; c) $BF_3.OEt_2$, MeOH; d) n-BuLi, i-$Pr_2NH$, petroleum ether 40-60; e) p-benzoquinone, THF; f) NaOAc, MeOH; g) 1. trialkylsilyl-acetylene (e.g. wherein R is ethyl), n-BuLi, $Et_2O$, THF; 2. $SnCl_2$, 10% HCl.

The process according to FIG. 3 is explained in detail below. However, the educts and the reagents and exact reaction conditions for each step may be varied by the skilled person based on general knowledge.
Preparation of the Educts (2) and (3):

The synthesis of the two starting materials, i.e. the 4,7-disubstituted isobenzofuran-1,3-dione (2) used in step a1) and the 1,2-bis(hydroxy-methyl)-3,6-disubstituted benzene (3) used in step a2) or a3), has already been reported in the literature 3.[7] The steps are a Diels-Alder reaction,[7,8] an acid-catalysed dehydration of the resultant cycloadduct 1,[7, 8] and a reduction of the anhydride 2 to the diol 3.[7,9].

Thus, a preferred embodiment of the present invention relates to a process as described above and below, wherein the educt (2) of step a1) and the educt (3) of steps a2) and a3) are prepared by the following steps:
x1) reacting 2,5-disubstituted furan with maleic anhydride by Diels-Alder cycloaddition to form a cycloadduct (1),
x2) dehydrating the product (1) of step x1) in the presence of an acid to form a 4,7-disubstituted isobenzofuran-1,3-dione (2),
and, in case of preparing (3),
x3) reduction of the product (2) of step x2) in the presence of a hydride reagent to form 1,2-bis(hydroxymethyl)-3,6-disubstituted benzene (3).

Figure 4:
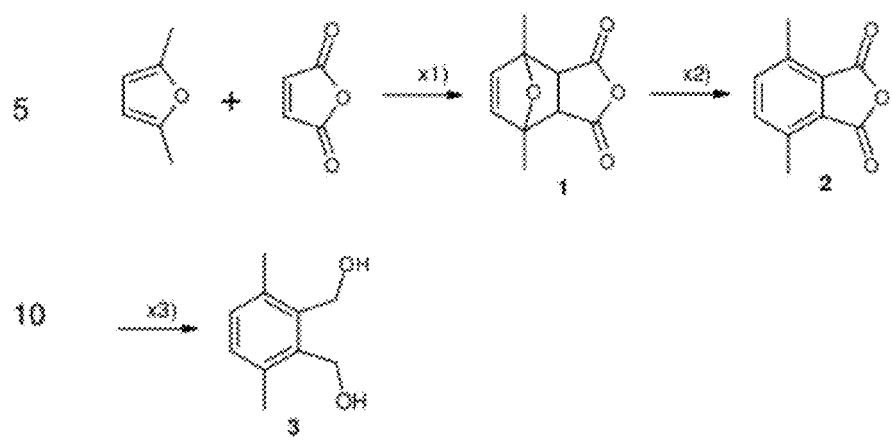
FIG. 4 shows a method for preparing the starting materials for the process according to the present invention.

FIG. 4 shows a preferred method for preparing (2) and (3). The starting materials 2,5-dimethylfuran and maleic anhydride are both commercially available. The reagents used in the process steps shown in FIG. 4 are as follows: x1) $Et_2O$; x2) conc. $H_2SO_4$; x3) $LiAlH_4$, THF.

Step a1): Reduction to
4,7-Dimethyl-3H-isobenzofuran-1-one 4

Anhydride 2 can be selectively reduced to the lactone 4 by two methods. Firstly, the reduction is effected by the use of a more selective reducing agent, which is preferably a hydride agent like for example sodium borohydride.[10] Alternatively, using a modified Yang-Zhu reduction[11] as described by Rainbolt et al, [12] anhydride 2 is reduced using zinc in acetic acid at 100° C. to yield the lactone 4.

Preferred reducing reagents include for example $NaBH_4$, Zn—HOAc, $H_2$—Pt, or $RuCl_2(PPh_3)_2$. Preferred solvents for this step include for example THF, dioxane, acetic acid, alcohol. The reaction temperature can be varied depending on the solvent and the reagents. Suitable temperatures are e.g. 23° C., 70° C. 90° C., or 100° C.

Step a2): Oxidation to prepare
4,7-Dimethyl-3H-isobenzofuran-1-one 4

From the previously reported diol 3,[7,9] the next step is an oxidation using an oxidising agent, like e.g. manganese(IV) oxide, based upon the method of Hirano et al who prepared 3H-isobenzofuran-1-one with this method.[13] Preferably, a large excess of oxidizing agent is employed, typically 10 equivalents, in order for complete conversion to the desired lactone product 4. If lower quantities of oxidizing agent are used, a mixture of lactone and lactol products is obtained.

Preferred oxidising agents include for example manganese (IV) oxide or pyridinium chlorochromate. Preferred solvents for this step include for example DCM or alcohols. The reaction temperature can be varied depending on the solvent and the reagents. Suitable temperatures are e.g. 23° C., 40° C. or 70° C.

Step a3): Oxidation to prepare
1-Hydroxy-4,7-dimethyl-1,3-dihydro-isobenzofuran
5a Diol 3 can be selectively oxidized to the lactol 5a using the method described by Corey et al which employs 2-iodoxybenzoic acid (IBX) as the oxidizing agent.[16] Typically for 1,4-diols like 3, further oxidation to the lactone does not occur to a significant degree.[16]

Preferred oxidizing agents include for example 2-iodoxybenzoic acid (IBX). Preferred solvents for this step include for example DMSO. The reaction temperature can be varied depending on the solvent and the reagents. A suitable temperature is e.g. 23° C.

Steps b), c): Reduction and methylation to prepare
1-Methoxy-4,7-dimethyl-1,3-dihydro-isobenzofuran
5b Lactone 4 is selectively reduced to the lactol 5a in the presence of a reducing agent, following the method described by Rainbolt et al which uses diisobutylaluminium hydride at −60° C.,[12] also known as Rodrigo's conditions.[14] After isolation, the lactol 5a is reacted with a methylation agent, like e.g. methanol, in the presence of a a Lewis acid catalyst, like e.g. boron trifluoride diethyl etherate, to yield the methylated lactol 5b, following the method of Man et al who prepared 1-methoxy-1,3-dihydro-isobenzofuran in this manner [15]

Preferred reducing agents for step b) include for example diisobutylaluminium hydride. Preferred solvents for step b) include for example DCM, $Et_2O$, toluene or mixtures thereof. The reaction temperature in step b) can be varied depending on the solvent and the reagents. Suitable temperatures are e.g. −78° C. or −60° C.

Preferred methylation reagents for step c) include for example $BF_3.OEt_2$-MeOH. Preferred solvents for step c) include for example methanol. The reaction temperature in step c) can be varied depending on the solvent and the reagents. Suitable temperatures are e.g. 0° C. or 23° C.

Steps d), e): Formation of 4,7-dimethyl-isobenzofuran 6 and Diels-Alder reaction to prepare 1,4,8,11-Tetramethyl-5,14,7,12-diepoxy-5,7,12,14-octahydropentacene-6,13-dione 7

From the methylated lactol 5b, the critical isobenzofuran intermediate, 4,7-dimethyl-isobenzofuran 6, is formed by treatment with lithium diisopropylamide in an analogous manner to that reported by Naito and Rickborn for the preparation of isobenzofuran.[17] A method of forming isobenzofuran from 2-(dimethoxymethyl)benzyl alcohol under acidic conditions has also been reported by Smith and Dibble[6] Isobenzofuran 6 is relatively stable and there are reports on the stability of similar derivatives,[18] nevertheless isobenzofuran 6 is kept in dilute solution rather than concentrated to dryness, and is used in the subsequent Diels-Alder reaction as rapidly as possible. In the Diels-Alder reaction, isobenzofuran 6 is reacted with p-benzoquinone to yield the bis-cycloadduct 7. Unlike the report of Dibble and Smith where acidic conditions are used,[6] in the present invention the product isolated still contains the epoxy bridges and has not undergone dehydration to yield the pentacenequinone product.

Preferred reagents for step d) include for example lithium diisopropylamide. Preferred solvents for step d) include for example petroleum distillates. The reaction temperature in step d) can be varied depending on the solvent and the reagents. Suitable temperatures are e.g. 0° C. or 23° C.

The preferred reactant for step e) is p-benzoquinone. Preferred solvents for step e) include for example petroleum distillates-THF. The reaction temperature in step e) can be varied depending on the solvent and the reagents. Suitable temperatures are e.g. 23° C. or 70° C.

Step f): Dehydration to prepare
1,4,8,11-Tetramethyl-6,13-pentacenequinone 8

In order to remove the epoxy bridges to form the pentacenequinone 8, bis-cycloadduct 7 is dehydrated under mildly basic conditions using sodium acetate in methanol in an similar manner to that reported by Wong et al.[14] It has been found that, when the reaction is performed in a microwave-reactor, at temperatures above the boiling point of the solvent (160° C.), high conversion to product can be obtained in short reactions time (5 mins), as opposed to prolonged reaction times at reflux temperature. Efforts to carry this dehydration out under acidic conditions using concentrated sulphuric acid at 0° C.[8] and concentrated hydrochloric acid in refluxing methanol[20] were both unsuccessful.

Preferred reagents for step f) include for example NaOAc. Preferred solvents for step f) include for example methanol. The reaction temperature in step f) can be varied depending on the solvent and the reagents. Suitable temperatures are e.g. 70° C. or higher temperatures Step g) Alkynation and aromatisation to prepare 1,4,8,11-Tetramethyl-6,13-bis(trialkylsilylethynyl)pentacene 9

Finally, the alkynation of pentacenequinone 8 is performed by reaction with lithium trialkylsilylacetylide (e.g. wherein alkyl is ethyl), formed in-situ from trialkylsilylacetylene and n-butyllithium, in an analogous manner to that described by Anthony and co-workers.[5] The intermediate species is then treated with an acidified saturated aqueous solution of tin(II) chloride to afford the final product material, 1,4,8,11-tetramethyl-6,13-bis(trialkylsilylethynyl)pentacene 9, in an analogous manner to that described by Anthony and co-workers.[4] Alternatively, arylacetylene moieties can be introduced into the pentacene species by reaction of pentacenequinone 8 with lithium arylacetylide, formed in-situ from arylacetylene and n-butyllithium, in an analogous manner to that described by Anthony and co-workers.[5]

Preferred reagents for step g) include for example: n-BuLi-trialkylsilylacetylene (e.g. n-BuLi-triethylsilylacetylene, n-BuLi-triisopropylacetylene) and n-BuLi-arylacetylene (e.g. n-BuLi-4-alkyl- or alkoxyphenylacetylene, n-BuLi-2,5-dialkyl- or dialkoxyphenylacetylene, n-BuLi-2,4,5-trialkyl or trialkoxyphenylacetylene, n-BuLi-2,4,6-trialkyl- or trialkoxyphenylacetylene, n-BuLi-5-alkylthiophenylacetylene, n-BuLi-2,4,5- or 2,4,6-trifluorophenylacetylene), followed by $SnCl_2$-HCl. Preferred solvents for step g) include for example $Et_2O$, THF, dioxane or mixtures thereof. The reaction temperature in step g) can be varied depending on the solvent and the reagents. Suitable temperatures are e.g. 0° C. or 23° C.

In a preferred embodiment of the present invention, the reduction of anhydride 2 to lactone 4 is carried out in one step (a1).

In another preferred embodiment of the present invention, the oxidation of diol 3 to lactol 5b is carried out in one step (a3), very preferably using 2-iodoxybenzoic acid (IBX).[17]

In another preferred embodiment of the present invention, the dehydration of bis-cycloadduct 7 (step f) is carried out in a sealed reactor vessel at elevated temperature and pressure, rather than in a microwave reactor.

The process according to the present invention has been described above for the preparation of 1,4,8,11-tetramethyl-6,13-bis(trialkylsilylethynyl) pentacene 9. However, it is also possible to prepare other 1,4,8,11-substituted bis(trialkylethynyl)pentacenes, like those of formula Ia shown below, or 1,4,8,11-substituted bis(arylethynyl)-pentacenes, like those of formula Ib shown below. This has been made possible by using the novel route of the present invention, due to the issue of the dicarboxyaldehyde intermediate.

The compounds obtainable or obtained by the process according to the present invention, and the novel compounds claimed in this invention, are preferably selected of formula I:

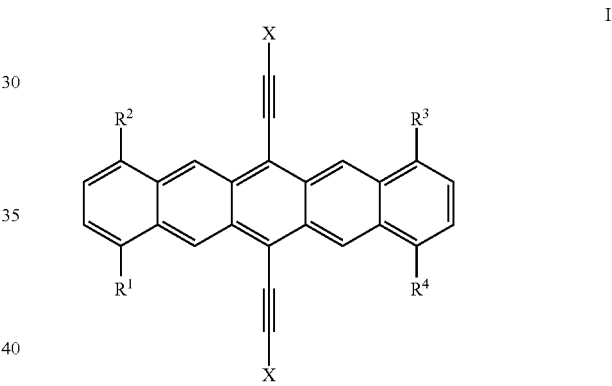

I wherein
X is $SiR^5R^6R^7$ or Ar,
$R^{1-7}$ are identical or different carbyl or hydrocarbyl groups,
Ar is in each occurrence independently of one another an optionally substituted aryl or heteroaryl group.

Especially preferred are compounds of the following formulae:

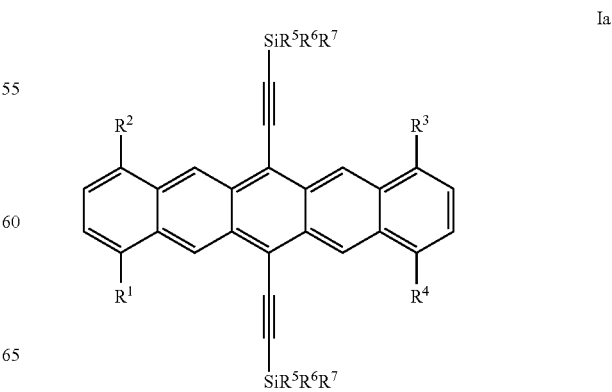

Ia

-continued

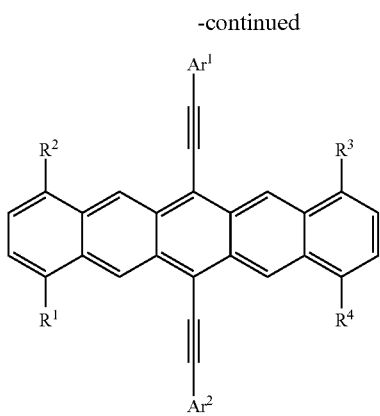

Ib wherein $R^{1-7}$ are as defined in formula I and $Ar^1$ and $Ar^2$ are identical or different, preferably identical, aromatic or heteroaromatic ring systems.

Preferred groups $Ar^{1,2}$ are 4-substituted-phenyl or 2,4,6-trisubstituted-phenyl, very preferably 4-alkylphenyl or 2,4,6-trialkylphenyl.

$R^{1-4}$ are identical or different carbyl or hydrocarbyl groups, preferably selected from straight-chain or branched $C_{1-12}$ alkyl, fluoroalkyl or alkoxy, F, Cl, cyano, most preferably straight-chain $C_{1-12}$ alkyl, especially preferably methyl, ethyl, propyl, butyl, pentyl, hexyl, heptyl, octyl, or F.

$R^{5-7}$ are identical or different carbyl or hydrocarbyl groups, preferably selected from straight-chain or branched $C_{1-12}$ alkyl. Most preferably $SiR^5R^6R^7$ is selected from tert-butyldimethylsilyl ($R^5=R^6=Me$, $R^7=t-Bu$), trimethylsilyl ($R^5=R^6=R^7=Me$), triisopropylsilyl ($R^5=R^6=R^7=i-Pr$), or triethylsilyl ($R^5=R^6=R^7=Et$).

The term "carbyl group" as used above and below denotes any monovalent or multivalent organic radical moiety which comprises at least one carbon atom either without any non-carbon atoms (like for example —C≡C—), or optionally combined with at least one non-carbon atom such as N, O, S, P, Si, Se, As, Te or Ge (for example carbonyl etc.). The term "hydrocarbyl group" denotes a carbyl group that does additionally contain one or more H atoms and optionally contains one or more hetero atoms like for example N, O, S, P, Si, Se, As, Te or Ge.

A carbyl or hydrocarbyl group comprising a chain of 3 or more C atoms may also be straight-chain, branched and/or cyclic, including spiro and/or fused rings.

Preferred carbyl and hydrocarbyl groups include alkyl, alkoxy, alkylcarbonyl, alkoxycarbonyl, alkylcarbonyloxy and alkoxycarbonyloxy, each of which is optionally substituted and has 1 to 40, preferably 1 to 25, very preferably 1 to 18 C atoms, furthermore optionally substituted aryl or aryloxy having 6 to 40, preferably 6 to 25 C atoms, furthermore alkylaryloxy, arylcarbonyl, aryloxycarbonyl, arylcarbonyloxy and aryloxycarbonyloxy, each of which is optionally substituted and has 6 to 40, preferably 7 to 40 C atoms, wherein all these groups optionally contain one or more hetero atoms, especially selected from N, O, S, P, Si, Se, As, Te and Ge.

The carbyl or hydrocarbyl group may be a saturated or unsaturated acyclic group, or a saturated or unsaturated cyclic group. Unsaturated acyclic or cyclic groups are preferred, especially aryl, alkenyl and alkynyl groups (especially ethynyl). Where the $C_1-C_{40}$ carbyl or hydrocarbyl group is acyclic, the group may be straight-chain or branched. The $C_1-C_{40}$ carbyl or hydrocarbyl group includes for example: a $C_1-C_{40}$ alkyl group, a $C_2-C_{40}$ alkenyl group, a $C_2-C_{40}$ alkynyl group, a $C_3-C_{40}$ alkyl group, a $C_4-C_{40}$ alkyldienyl group, a $C_4-C_{40}$ polyenyl group, a $C_6-C_{18}$ aryl group, a $C_6-C_{40}$ alkylaryl group, a $C_6-C_{40}$ arylalkyl group, a $C_4-C_{40}$ cycloalkyl group, a $C_4-C_{40}$ cycloalkenyl group, and the like. Preferred among the foregoing groups are a $C_1-C_{20}$ alkyl group, a $C_2-C_{20}$ alkenyl group, a $C_2-C_{20}$ alkynyl group, a $C_3-C_{20}$ alkyl group, a $C_4-C_{20}$ alkyldienyl group, a $C_6-C_{12}$ aryl group and a $C_4-C_{20}$ polyenyl group, respectively. Also included are combinations of groups having carbon atoms and groups having hetero atoms, like e.g. an alkynyl group, preferably ethynyl, that is substituted with a silyl group, preferably a trialkylsilyl group.

Aryl and heteroaryl preferably denote a mono-, bi- or tri-cyclic aromatic or heteroaromatic group with up to 25 C atoms that may also comprise condensed rings and is optionally substituted with one or more groups L, wherein L is F, Cl, Br, I or an alkyl, alkoxy, alkylcarbonyl or alkoxycarbonyl group with 1 to 12 C atoms, wherein one or more H atoms may be replaced by F or Cl.

Especially preferred aryl and heteroaryl groups are phenyl in which, in addition, one or more CH groups may be replaced by N, naphthalene, thiophene, selenophene thienothiophene, dithienothiophene, fluorene and oxazole, all of which can be unsubstituted, mono- or polysubstituted with L as defined above.

In formula I $R^{1-7}$ preferably denotes straight chain, branched or cyclic alkyl with 1 to 20 C-atoms, which is unsubstituted or mono- or polysubstituted by F, Cl, Br or I, and wherein one or more non-adjacent $CH_2$ groups are optionally replaced, in each case independently from one another, by —O—, —S—, —NR°—, —SiR°R°°—, —CY$^1$=CY$^2$— or —C≡C— in such a manner that O and/or S atoms are not linked directly to one another, or denotes optionally substituted aryl or heteroaryl preferably having 1 to 30 C-atoms, with R° and R°° being independently of each other H or alkyl with 1 to 12 C-atoms, $Y^1$ and $Y^2$ being independently of each other H, F, Cl or CN, If $R^{1-7}$ is an alkyl or alkoxy radical, i.e. where the terminal $CH_2$ group is replaced by —O—, this may be straight-chain or branched. It is preferably straight-chain, has 2 to 8 carbon atoms and accordingly is preferably ethyl, propyl, butyl, pentyl, hexyl, heptyl, octyl, ethoxy, propoxy, butoxy, pentoxy, hexyloxy, heptoxy, or octoxy, furthermore methyl, nonyl, decyl, undecyl, dodecyl, tridecyl, tetradecyl, pentadecyl, nonoxy, decoxy, undecoxy, dodecoxy, tridecoxy or tetradecoxy, for example. Especially preferred are n-hexyl and n-dodecyl.

If $R^{1-7}$ is an alkyl group wherein one or more $CH_2$ groups are replaced by —CH=CH—, this may be straight-chain or branched. It is preferably straight-chain, has 2 to 12 C-atoms and accordingly is preferably vinyl, prop-1-, or prop-2-enyl, but-1-, 2- or but-3-enyl, pent-1-, 2-, 3- or pent-4-enyl, hex-1-, 2-, 3-, 4- or hex-5-enyl, hept-1-, 2-, 3-, 4-, 5- or hept-6-enyl, oct-1-, 2-, 3-, 4-, 5-, 6- or oct-7-enyl, non-1-, 2-, 3-, 4-, 5-, 6-, 7- or non-8-enyl, dec-1-, 2-, 3-, 4-, 5-, 6-, 7-, 8- or dec-9-enyl, undec-1-, 2-, 3-, 4-, 5-, 6-, 7-, 8-, 9- or undec-10-enyl, dodec-1-, 2-, 3-, 4-, 5-, 6-, 7-, 8-, -9, -10 or undec-11-enyl. The alkenyl group may comprise C=C-bonds with E- or Z-configuration or a mixture thereof.

If $R^{1-7}$ is oxaalkyl, i.e. where one $CH_2$ group is replaced by —O—, is preferably straight-chain 2-oxapropyl (=methoxymethyl), 2-(=ethoxymethyl) or 3-oxabutyl (=2-methoxyethyl), 2-, 3-, or 4-oxapentyl, 2-, 3-, 4-, or 5-oxahexyl, 2-, 3-, 4-, 5-, or 6-oxaheptyl, 2-, 3-, 4-, 5-, 6- or 7-oxaoctyl, 2-, 3-, 4-, 5-, 6-, 7- or 8-oxanonyl or 2-, 3-, 4-, 5-, 6-,7-, 8- or 9-oxadecyl, for example.

If $R^{1-7}$ is thioalkyl, i.e where one $CH_2$ group is replaced by —S—, is preferably straight-chain thiomethyl (—SCH$_3$), 1-thioethyl (—SCH$_2$CH$_3$), 1-thiopropyl (=—SCH$_2$CH$_2$CH$_3$), 1-(thiobutyl), 1-(thiopentyl), 1-(thiohexyl), 1-(thioheptyl), 1-(thiooctyl), 1-(thiononyl), 1-(thiodecyl), 1-(thioundecyl) or 1-(thiododecyl), wherein preferably the CH$_2$ group adjacent to the sp$^2$ hybridised vinyl carbon atom is replaced.

If R$^{1-7}$ is fluoroalkyl, it is preferably straight-chain perfluoroalkyl wherein i is an integer from 1 to 15, in particular CF$_3$, C$_2$F$_5$, C$_3$F$_7$, C$_4$F$_9$, C$_5$F$_{11}$, C$_6$F$_{13}$, C$_7$F$_{15}$ or C$_8$F$_{17}$, very preferably C$_6$F$_{13}$.

Very preferably R$^{1-7}$ is selected from C$_1$-C$_{20}$-alkyl that is optionally substituted with one or more fluorine atoms, C$_1$-C$_{20}$-alkenyl, C$_1$-C$_{20}$-alkynyl, C$_1$-C$_{20}$-alkoxy, C$_1$-C$_{20}$-thioalkyl, C$_1$-C$_{20}$-silyl, C$_1$-C$_{20}$-amino or C$_1$-C$_{20}$-fluoroalkyl, in particular from alkenyl, alkynyl, alkoxy, thioalkyl or fluoroalkyl, all of which are straight-chain and have 1 to 12, preferably 5 to 12 C-atoms, most preferably pentyl, hexyl, heptyl, octyl, nonyl, decyl, undecyl or dodecyl.

—CY$^1$=CY$^2$— is preferably —CH=CH—, —CF=CF— or —CH=C(CN)—.

R$^{5-7}$ are preferably identical or different groups selected from a C$_1$-C$_{40}$-alkyl group, preferably C$_1$-C$_4$-alkyl, most preferably methyl, ethyl, n-propyl or isopropyl, a C$_6$-C$_{40}$-aryl group, preferably phenyl, a C$_6$-C$_{40}$-arylalkyl group, a C$_1$-C$_{40}$-alkoxy group, or a C$_6$-C$_{40}$-arylalkyloxy group, wherein all these groups are optionally substituted for example with one or more halogen atoms. Preferably, R$^{6-7}$ are each independently selected from optionally substituted C$_{1-12}$-alkyl, more preferably C$_{1-4}$-alkyl, most preferably C$_{1-3}$-alkyl, for example isopropyl, and optionally substituted C$_{6-10}$-aryl, preferably phenyl. Further preferred is a silyl group of formula —SiR$^5$R$^6$ wherein R$^6$ forms a cyclic silyl alkyl group together with the Si atom, preferably having 1 to 8 C atoms.

In one preferred embodiment R$^{5-7}$ are identical groups, for example identical, optionally substituted, alkyl groups, as in triisopropylsilyl. Very preferably R$^{5-7}$ are identical, optionally substituted C$_{1-10}$, more preferably C$_{1-4}$, most preferably C$_{1-3}$ alkyl groups. A preferred alkyl group in this case is isopropyl.

Preferred groups —SiR$^5$R$^6$R$^7$ include, without limitation, trimethylsilyl, triethylsilyl, tripropylsilyl, dimethylethylsilyl, diethylmethylsilyl, dimethylpropylsilyl, dimethylisopropylsilyl, dipropylmethylsilyl, diisopropylmethylsilyl, dipropylethylsilyl, diisopropylethylsilyl, diethylisopropylsilyl, triisopropylsilyl, trimethoxysilyl, triethoxysilyl, triphenylsilyl, diphenylisopropylsilyl, diisopropylphenylsilyl, diphenylethylsilyl, diethylphenylsilyl, diphenylmethylsilyl, triphenoxysilyl, dimethylmethoxysilyl, dimethylphenoxysilyl, methylmethoxyphenylsilyl, etc., wherein the alkyl, aryl or alkoxy group is optionally substituted.

The compounds according to the present invention are useful as charge transport, semiconducting, electrically conducting, photoconducting or light emitting materials in optical, electrooptical, electronic, electroluminescent or photoluminescent components or devices.

Especially preferred devices are OFETs, TFTs, ICs, logic circuits, capacitors, RFID tags, OLEDs, OLETs, OPVs, solar cells, laser diodes, photoconductors, photodetectors, electrophotographic devices, electrophotographic recording devices, organic memory devices, sensor devices, charge injection layers, Schottky diodes, planarising layers, antistatic films, conducting substrates and conducting patterns. In these devices, the polymers of the present invention are typically applied as thin layers or films.

OFETs where an organic semiconducting (OSC) material is arranged as a thin film between a gate dielectric and a drain and a source electrode, are generally known, and are described for example in U.S. Pat. No. 5,892,244, WO 00/79617, U.S. Pat. No. 5,998,804, and in the references cited in the background section. Due to the advantages, like low cost production using the solubility properties of the polymers according to the invention and thus the processibility of large surfaces, preferred applications of these FETs are such as integrated circuitry, TFT displays and security applications.

Another aspect of the invention relates to a formulation comprising one or more substituted pentacene compounds as described above and below and one or more organic solvents.

Examples of suitable and preferred organic solvents include, without limitation, dichloromethane, trichloromethane, monochlorobenzene, o-dichlorobenzene, tetrahydrofuran, anisole, morpholine, toluene, o-xylene, m-xylene, p-xylene, 1,4-dioxane, acetone, methylethylketone, 1,2-dichloroethane, 1,1,1-trichloroethane, 1,1,2,2-tetrachloroethane, ethyl acetate, n-butyl acetate, dimethylformamide, dimethylacetamide, dimethylsulfoxide, tetraline, decaline, indane, methyl benzoate, ethyl benzoate, mesitylene and/or mixtures thereof.

The concentration of the substituted pentacene compounds in the formulation is preferably from 1% to 10% by weight, more preferably from 1% to 5% by weight.

Optionally, the formulation also comprises one or more organic binders, to adjust the rheological properties, as described for example in WO 2005/055248 A2.

Preferred polymeric binders include, without limitation, polystyrene, poly(α-methylstyrene), poly(α-vinylnaphtalene), poly(vinyltoluene), polyethylene, cis-polybutadiene, polypropylene, polyisoprene, poly(4-methyl-1-pentene), poly(4-methylstyrene), poly(chorotrifluoroethylene), poly (2-methyl-1,3-butadiene), poly(p-xylylene), poly(α-α-α'-α' tetrafluoro-p-xylylene), poly[1,1-(2-methyl propane)bis(4-phenyl)carbonate], poly(cyclohexyl methacrylate), poly (chlorostyrene), poly(2,6-dimethyl-1,4-phenylene ether), polyisobutylene, poly(vinyl cyclohexane), poly(vinylcinnamate), poly(4-vinylbiphenyl), poly(1,3-butadiene), polyphenylene. Further preferred are copolymers, including regular, random or block copolymers like poly(ethylene/tetrafluoroethylene), poly(ethylene/chlorotrifluoro-ethylene), fluorinated ethylene/propylene copolymer, polystyrene-co-α-methylstyrene, ethylene/ethyl acrylate copolymer, poly (styrene/10% butadiene), poly(styrene/15% butadiene), poly (styrene/2,4 dimethylstyrene) or the Topas® series (from Ticona).

Further preferred are polymeric semiconducting binders like polytriarylamine (PTAA), polythiophene, polyfluorene, polyspirobifluorene, wherein the monomer units are optionally substituted with carbyl or hydrocarbyl groups.

The proportions of binder to polyacene in the formulation are typically 20:1 to 1:20 by weight, preferably 10:1 to 1:10 more preferably 5:1 to 1:5, still more preferably 3:1 to 1:3 further preferably 2:1 to 1:2 and especially 1:1

The total solids content (i.e. substituted pentacene compound and binder) in the formulation is preferably from 0.1 to 15% by weight, more preferably from 0.5 to 10% by weight.

After the appropriate mixing and ageing, solutions are evaluated as one of the following categories: complete solution, borderline solution or insoluble. The contour line is drawn to outline the solubility parameter-hydrogen bonding limits dividing solubility and insolubility. 'Complete' solvents falling within the solubility area can be chosen from literature values such as published in "Crowley, J. D., Teague, G. S. Jr and Lowe, J. W. Jr., Journal of Paint Technology, 38, No 496, 296 (1966)". Solvent blends may also be used and can be identified as described in "Solvents, W. H. Ellis, Federation of Societies for Coatings Technology, p 9-10, 1986". Such a procedure may lead to a blend of 'non' solvents that will dissolve both the compounds of the present invention, although it is desirable to have at least one true solvent in a blend.

The compounds according to the present invention can also be used in patterned OSC layers in the devices as described above and below. For applications in modern microelectronics it is generally desirable to generate small structures or patterns to reduce cost (more devices/unit area), and power consumption. Patterning of thin layers comprising a compound according to the present invention can be carried out for example by photolithography, electron beam lithography or laser patterning.

For use as thin layers in electronic or electrooptical devices the compounds and formulations of the present invention may be deposited by any suitable method. Liquid coating of devices is more desirable than vacuum deposition techniques. Solution deposition methods are especially preferred. The formulations of the present invention enable the use of a number of liquid coating techniques. Preferred deposition techniques include, without limitation, dip coating, spin coating, ink jet printing, letter-press printing, screen printing, doctor blade coating, roller printing, reverse-roller printing, offset lithography printing, flexographic printing, web printing, spray coating, brush coating or pad printing. Ink-jet printing is particularly preferred as it allows high resolution layers and devices to be prepared.

Selected formulations of the present invention may be applied to prefabricated device substrates by ink jet printing or microdispensing. Preferably industrial piezoelectric print heads such as but not limited to those supplied by Aprion, Hitachi-Koki, InkJet Technology, On Target Technology, Picojet, Spectra, Trident, Xaar may be used to apply the organic semiconductor layer to a substrate. Additionally semi-industrial heads such as those manufactured by Brother, Epson, Konica, Seiko Instruments Toshiba TEC or single nozzle microdispensers such as those produced by Microdrop and Microfab may be used.

In order to be applied by ink jet printing or microdispensing, the compounds should be first dissolved in a suitable solvent. Solvents must fulfil the requirements stated above and must not have any detrimental effect on the chosen print head. Additionally, solvents should have boiling points >100° C., preferably >140° C. and more preferably >150° C. in order to prevent operability problems caused by the solution drying out inside the print head. Apart from the solvents methoned above, suitable solvents include substituted and non-substituted xylene derivatives, di-$C_{1-2}$-alkyl formamide, substituted and non-substituted anisoles and other phenol-ether derivatives, substituted heterocycles such as substituted pyridines, pyrazines, pyrimidines, pyrrolidinones, substituted and non-substituted N,N-di-$C_{1-2}$-alkylanilines and other fluorinated or chlorinated aromatics.

A preferred solvent for depositing a compound according to the present invention by ink jet printing comprises a benzene derivative which has a benzene ring substituted by one or more substituents wherein the total number of carbon atoms among the one or more substituents is at least three. For example, the benzene derivative may be substituted with a propyl group or three methyl groups, in either case there being at least three carbon atoms in total. Such a solvent enables an ink jet fluid to be formed comprising the solvent with the compound, which reduces or prevents clogging of the jets and separation of the components during spraying. The solvent(s) may include those selected from the following list of examples: dodecylbenzene, 1-methyl-4-tert-butylbenzene, terpineol limonene, isodurene, terpinolene, cymene, diethylbenzene. The solvent may be a solvent mixture, that is a combination of two or more solvents, each solvent preferably having a boiling point >100° C., more preferably >140° C. Such solvent(s) also enhance film formation in the layer deposited and reduce defects in the layer.

The ink jet fluid (that is mixture of solvent, binder and semiconducting compound) preferably has a viscosity at 20° C. of 1-100 mPa·s, more preferably 1-50 mPa·s and most preferably 1-30 mPa·s.

The compounds or formulations according to the present invention can additionally comprise one or more further components like for example surface-active compounds, lubricating agents, wetting agents, dispersing agents, hydrophobing agents, adhesive agents, flow improvers, defoaming agents, deaerators, diluents which may be reactive or non-reactive, auxiliaries, colourants, dyes or pigments, sensitizers, stabilizers, nanoparticles or inhibitors.

An OFET device according to the present invention preferably comprises:

a source electrode (4), a drain electrode (4), a gate electrode (2), an organic semiconducting (OSC) layer (5), one or more gate insulator layers (3), optionally a substrate (1), wherein the OSC layer comprises one or more substituted pentacene compounds according to the present invention.

The gate, source and drain electrodes and the insulating and semiconducting layer in the OFET device may be arranged in any sequence, provided that the source and drain electrode are separated from the gate electrode by the insulating layer, the gate electrode and the semiconductor layer both contact the insulating layer, and the source electrode and the drain electrode both contact the semiconducting layer. The OFET device can be a top gate device or a bottom gate device. Suitable structures and manufacturing methods of an OFET device, and suitable methods for measuring the device performance are known to the skilled in the art and are described in the literature, for example in WO 03/052841 A1 and WO 2005/055248 A2.

Figure 5:
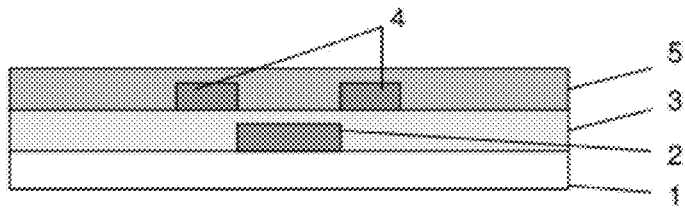
FIG. 5 exemplarily shows a bottom gate OFET according to the present invention.

FIG. 5 exemplarily depicts a bottom gate (BG), bottom contact (BC) OFET device according to the present invention, comprising a substrate (1), a gate electrode (2), a dielectric layer (3), source and drain electrodes (4), and an OSC layer (5).

Such a device can be prepared by a process comprising the steps of applying a gate electrode (2) on a substrate (1), applying a dielectric layer (3) on top of the gate electrode (2) and the substrate (1), applying source and drain electrodes (4) on top of the dielectric layer (3), and applying an OSC layer (5) on top of the electrodes (4) and the dielectric layer (3).

Figure 6:
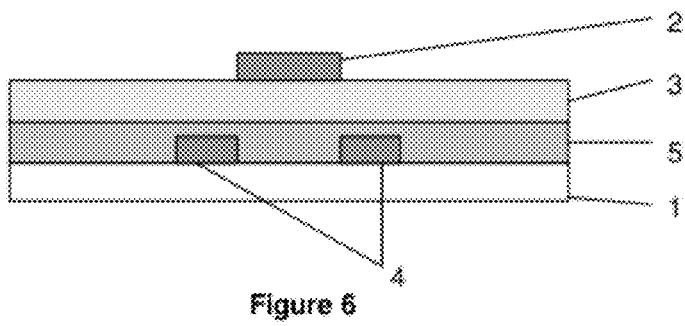
FIG. 6 exemplarily shows a top gate OFET according to the present invention.

FIG. 6 exemplarily depicts a top gate (TG) OFET device according to the present invention, comprising a substrate (1), source and drain electrodes (4), an OSC layer (5), a dielectric layer (3), and a gate electrode (2).

Such a device can be prepared by a process comprising the steps of applying source and drain electrodes (4) on a substrate (1), applying an OSC layer (5) on top of the electrodes (4) and the substrate (1), applying a dielectric layer (3) on top of the OSC layer (5), and applying a gate electrode (2) on top of the dielectric layer (3).

An OPV device according to the present invention preferably comprises:
- a low work function electrode (for example Aluminum),
- a high work function electrode (for example ITO), one of which is transparent,
- a bilayer of consisting of a hole transporting and an electron transporting material; the bilayer can exist as two distinct layers, or a blended mixture (see for example Coakley, K. M. and McGehee, M. D. *Chem. Mater.* 2004, 16, 4533),
- an optional conducting polymer layer (such as for example PEDOT:PSS) to modify the work function of the high work function electrode to provide an ohmic contact for the hole,
- an optional coating on the high workfunction electrode (such as LiF) to provide an ohmic contact for electrons.

The hole transporting material in the blend exists of one of the compounds of the present invention. The electron transporting material can be an inorganic material such as zinc oxide or cadmium selenide, or an organic material such as a fullerene derivate (for example PCBM, [(6,6)-phenyl C61-butyric acid methyl ester] or a polymer see for example Coakley, K. M. and McGehee, M. D. *Chem. Mater.* 2004, 16, 4533). If the bilayer is a blend an optional annealing step may be necessary to optimize device performance.

In security applications, OFETs and other devices with semiconducting materials according to the present invention, like transistors or diodes, can be used for RFID tags or security markings to authenticate and prevent counterfeiting of documents of value like banknotes, credit cards or ID cards, national ID documents, licenses or any product with monetry value, like stamps, tickets, shares, cheques etc.

Alternatively, the materials according to the invention can be used in organic light emitting devices or diodes (OLEDs), e.g., in display applications or as backlight of e.g. liquid crystal displays. Common OLEDs are realized using multilayer structures. An emission layer is generally sandwiched between one or more electron-transport and/or hole-transport layers. By applying an electric voltage electrons and holes as charge carriers move towards the emission layer where their recombination leads to the excitation and hence luminescence of the lumophor units contained in the emission layer. The inventive compounds, materials and films may be employed in one or more of the charge transport layers and/or in the emission layer, corresponding to their electrical and/or optical properties. Furthermore their use within the emission layer is especially advantageous, if the compounds, materials and films according to the invention show electroluminescent properties themselves or comprise electroluminescent groups or compounds. The selection, characterization as well as the processing of suitable monomeric, oligomeric and polymeric compounds or materials for the use in OLEDs is generally known by a person skilled in the art, see, e.g., Meerholz, Synthetic Materials, 111-112, 2000, 31-34, Alcala, J. Appl. Phys., 88, 2000, 7124-7128 and the literature cited therein.

According to another use, the materials according to the present invention, especially those which show photoluminescent properties, may be employed as materials of light sources, e.g., of display devices such as described in EP 0 889 350 A1 or by C. Weder et al., Science, 279, 1998, 835-837.

A further aspect of the invention relates to both the oxidised and reduced form of the polymers according to this invention. Either loss or gain of electrons results in formation of a highly delocalised ionic form, which is of high conductivity. This can occur on exposure to common dopants. Suitable dopants and methods of doping are known to those skilled in the art, e.g. from EP 0 528 662, U.S. Pat. No. 5,198,153 or WO 96/21659.

The doping process typically implies treatment of the semiconductor material with an oxidating or reducing agent in a redox reaction to form delocalised ionic centres in the material, with the corresponding counterions derived from the applied dopants. Suitable doping methods comprise for example exposure to a doping vapor in the atmospheric pressure or at a reduced pressure, electrochemical doping in a solution containing a dopant, bringing a dopant into contact with the semiconductor material to be thermally diffused, and ion-implantantion of the dopant into the semiconductor material.

When electrons are used as carriers, suitable dopants are for example halogens (e.g., $I_2$, $Cl_2$, $Br_2$, ICl, $ICl_3$, IBr and IF), Lewis acids (e.g., $PF_5$, $AsF_5$, $SbF_5$, $BF_3$, $BCl_3$, $SbCl_5$, $BBr_3$ and $SO_3$), protonic acids, organic acids, or amino acids (e.g., HF, HCl, $HNO_3$, $H_2SO_4$, $HClO_4$, $FSO_3H$ and $ClSO_3H$), transition metal compounds (e.g., $FeCl_3$, FeOCl, $Fe(ClO_4)_3$, $Fe(4-CH_3C_6H_4SO_3)_3$, $TiCl_4$, $ZrCl_4$, $HfCl_4$, $NbF_5$, $NbCl_5$, $TaCl_5$, $MoF_5$, $MoCl_5$, $WF_5$, $WCl_6$, $UF_6$ and $LnCl_3$ (wherein Ln is a lanthanoid), anions (e.g., $Cl^-$, $Br^-$, $I^-$, $HSO_4^-$, $SO_4^{2-}$, $NO_3^-$, $ClO_4^-$, $BF_4^-$, $PF_6^-$, $AsF_6^-$, $SbF_6^-$, $FeCl_4^-$, $Fe(CN)_6^{3-}$, and anions of various sulfonic acids, such as aryl-$SO_3^-$). When holes are used as carriers, examples of dopants are cations (e.g., $H^+$, $Li^+$, $Na^+$, $K^+$, $Rb^+$ and $Cs^+$), alkali metals (e.g., Li, Na, K, Rb, and Cs), alkaline-earth metals (e.g., Ca, Sr, and Ba), $O_2$, $XeOF_4$, $(NO_2^+)(SbF_6^-)$, $(NO_2^+)(SbCl_6^-)$, $(NO_2^+)(BF_4^-)$, $AgClO_4$, $H_2IrCl_6$, $La(NO_3)_3 \cdot 6H_2O$, $FSO_2OOSO_2F$, Eu, acetylcholine, $R_4N^+$, (R is an alkyl group), $R_4P^+$ (R is an alkyl group), $R_6As^+$ (R is an alkyl group), and $R_3S^+$ (R is an alkyl group).

The conducting form of the polymers of the present invention can be used as an organic "metal" in applications including, but not limited to, charge injection layers and ITO planarising layers in OLED applications, films for flat panel displays and touch screens, antistatic films, printed conductive substrates, patterns or tracts in electronic applications such as printed circuit boards and condensers.

According to another use, the materials according to the present invention can be used alone or together with other materials in or as alignment layers in LCD or OLED devices, as described for example in US 2003/0021913. The use of charge transport compounds according to the present invention can increase the electrical conductivity of the alignment layer. When used in an LCD, this increased electrical conductivity can reduce adverse residual dc effects in the switchable LCD cell and suppress image sticking or, for example in ferroelectric LCDs, reduce the residual charge produced by the switching of the spontaneous polarisation charge of the ferroelectric LCs. When used in an OLED device comprising a light emitting material provided onto the alignment layer, this increased electrical conductivity can enhance the electroluminescence of the light emitting material. The compounds or materials according to the present invention having mesogenic or liquid crystalline properties can form oriented anisotropic films as described above, which are especially useful as alignment layers to induce or enhance alignment in a liquid crystal medium provided onto said anisotropic film. The materials according to the present invention may also be combined with photoisomerisable compounds and/or chromophores for use in or as photoalignment layers, as described in US 2003/0021913.

According to another use the materials according to the present invention, especially their water-soluble derivatives (for example with polar or ionic side groups) or ionically doped forms, can be employed as chemical sensors or materials for detecting and discriminating DNA sequences. Such uses are described for example in L. Chen, D. W. McBranch, H. Wang, R. Helgeson, F. Wudl and D. G. Whitten, Proc. Natl. Acad. Sci. U.S.A. 1999, 96, 12287; D. Wang, X. Gong, P. S. Heeger, F. Rininsland, G. C. Bazan and A. J. Heeger, Proc. Natl. Acad. Sci. U.S.A. 2002, 99, 49; N. DiCesare, M. R. Pinot, K. S. Schanze and J. R. Lakowicz, Langmuir 2002, 18, 7785; D. T. McQuade, A. E. Pullen, T. M. Swager, Chem. Rev. 2000, 100, 2537.

Unless the context clearly indicates otherwise, as used herein plural forms of the terms herein are to be construed as including the singular form and vice versa.

Throughout the description and claims of this specification, the words "comprise" and "contain" and variations of the words, for example "comprising" and "comprises", mean "including but not limited to", and are not intended to (and do not) exclude other components.

It will be appreciated that variations to the foregoing embodiments of the invention can be made while still falling within the scope of the invention. Each feature disclosed in this specification, unless stated otherwise, may be replaced by alternative features serving the same, equivalent or similar purpose. Thus, unless stated otherwise, each feature disclosed is one example only of a generic series of equivalent or similar features.

All of the features disclosed in this specification may be combined in any combination, except combinations where at least some of such features and/or steps are mutually exclusive. In particular, the preferred features of the invention are applicable to all aspects of the invention and may be used in any combination. Likewise, features described in non-essential combinations may be used separately (not in combination).

LIST OF CITED REFERENCES

1. J. E. Anthony, J. S. Brooks, D. L. Eaton, S. R. Parkin, *J. Am. Chem. Soc.,* 2001, 123, 9482.
2. U.S. Pat. No. 6,690,029 B1.
3. C. D. Sheraw, T. N. Jackson, D. L. Eaton, J. E. Anthony, *Adv. Mat.,* 2003, 15, 2009.
4. J. E. Anthony, D. L. Eaton, S. R. Parkin, *Org. Lett.,* 2002, 4, 15.
5. C. R. Swartz, S. R. Parkin, J. E. Bullock, J. E. Anthony, A. C. Mayer, G. C. Malliaras, *Org. Lett.,* 2005, 7, 3163.
6. J. G. Smith, P. W. Dibble, *J. Org. Chem.,* 1983, 48, 5361.
7. Lachapelle, M. St-Jacques, *Can. J. Chem.* 1985, 63, 2185.
8. T.-L. Chan, T. C. W. Mak, C.-D. Poon, H. N. C. Wong, J. H. Jia, L. L. Wang, *Tetrahedron,* 1986, 42, 655.
9. G. M. Rubottom, J. E. Wey, *Synth. Comm.,* 1984, 14, 507.
10. K. Soai, S. Yokoyama, K. Mochida, *Synthesis,* 1987, 647.
11. C.-F. Yang, J.-L. Zhu, Huaxue Shijie, 2000, 41, 426.
12. J. E. Rainbolt, G. P. Miller, *J. Org. Chem.,* 2007, 72, 3020.
13. M. Hirano, S. Yakabe, H. Chikamori, J. H. Clark, T. Morimoto, *J. Chem. Res., Synopses,* 1998, 12, 770.
14. B. A. Keay, R. Rodrigo, *Can. J. Chem.,* 1985, 63, 735.
15. Y.-M. Man, T. C. W. Mak, H. N. C. Wong, *J. Org. Chem.,* 1990, 55, 3214.
16. E. J. Corey, A. Palani, *Tet. Lett.,* 1995, 36, 3485.
17. K. Naito, B. Rickborn, *J. Org. Chem.,* 1980, 45, 4061.
18. S. Miki, M. Yoshida, Z. Yoshida, *Tet. Lett.,* 1989, 30, 103.
19. H. N. C. Wong, T.-K. Ng, T.-Y. Wong, *Heterocycles,* 1984, 22, 875.
20. D. H. Kim, J. A. Lee, S. U. Son, Y. K. Chung, C. H. Choi, *Tet. Lett.,* 2005, 46, 4627.
21. D. Sparfel, F. Gobert, J. Rigaudy, *Tetrahedron.* 1980, 36, 2225.
22. A. Maliakal, K. Raghavachari, H. Katz, E. Chandross, T. Siegrist, *Chem. Mat.* 2004, 16, 4980.
23. WO 2005/055248 A2.

The invention is described in more detail by the following examples, which are illustrative only and do not limit the scope of the invention.

Example 1

1,4,8,11-Tetramethyl-6,13-bis(triethylsilylethynyl)pentacene (9) is prepared as described below.

1,7-Dimethyl-4,10-dioxa-tricyclo[5.2.1.0$^{2,6}$]dec-8-ene-3,5-dione 1

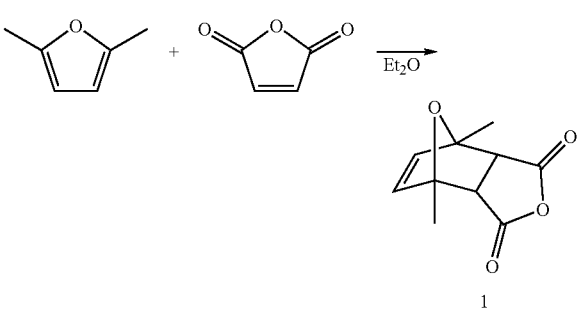

A 100 mL 3-necked RBF is fitted with a mechanical stirrer, a condenser and a subaseal, and placed under nitrogen. Maleic anhydride (25.5 g, 0.260 mol) and anhydrous diethyl ether (35 mL) are charged to the RBF. 2,5-Dimethylfuran (27.7 mL, 0.260 mol) is added via syringe over a period of 20 mins to the suspension at 22° C. The reaction mixture is stirred for 18 h. The product is filtered off, washed with cold diethyl ether (100 mL), and dried under vacuum to yield the product 1 as a cream solid (36.32 g, 72%): $^{1}$H-NMR (300 MHz, CDCl$_3$) δ6.35 (s, 2H), 3.16 (s, 2H), 1.76 (s, 6H).

4,7-Dimethyl-isobenzofuran-1,3-dione 2

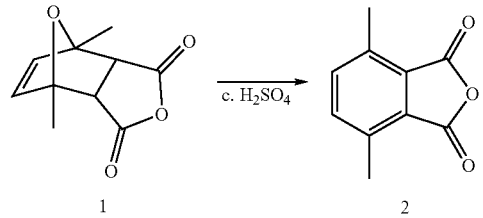

1,7-Dimethyl-4,10-dioxa-tricyclo[5.2.1.0]dec-8-ene-3,5-dione 1 (30.0 g, 0.150 mol) is added slowly in portions to stirred 98% sulfuric acid (300 mL) in a 1 L flange flask cooled to −5° C. using a salt-ice bath—note that the temperature is kept below 0° C. during the addition. The mixture is stirred for 30 mins at −5° C. and then allowed to warm up to 22° C. The mixture is carefully poured onto crushed ice (1.5 L). The cream precipitate that formed is filtered off and washed with ice water. The precipitate is dissolved in a 5% aq. sodium hydroxide solution (225 mL) with stirring. Glacial acetic acid (20 mL) is added slowly to the stirred solution. A cream precipitate forms and this is filtered off and discarded. 37% Hydrochloric acid (50 mL) is added to the stirred filtrate and the mixture is stirred for 2 h during which time a precipitate is formed. The precipitate is filtered off and dried in the vacuum oven overnight to yield the product as a cream solid (11.13 g, 41%). The filtrate is allowed to stand overnight during which time further product precipitated out. The second crop of precipitate is filtered off and dried under vacuum to yield the product 2 as a cream solid (5.79 g, 21%): $^1$H-NMR (300 MHz, CDCl$_3$) δ 7.18 (s, 2H), 2.40 (s, 6H).

1,2-Bis(hydroxymethyl)-3,6-dimethylbenzene 3

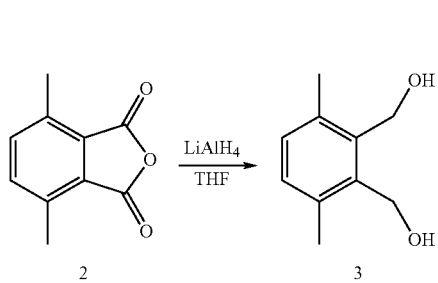

A 1 L 3-necked RBF is charged with a 1.0M lithium aluminium hydride solution in tetrahydrofuran (175 mL, 0.175 mol) and anhydrous tetrahydrofuran (100 mL) under nitrogen. The solution is cooled to −78° C. and a solution of 1,7-dimethyl-4,10-dioxa-tricyclo[5.2.1.0$^{2,6}$]dec-8-ene-3,5-dione 2 (12.3 g, 0.070 mol) in anhydrous tetrahydrofuran (150 mL) is added from a dropping funnel over a period of 30 minutes The reaction mixture is heated to reflux and stirred for 45 h. The reaction mixture is cooled to 0° C. using an ice bath and 2M sodium hydroxide solution (20 mL) is slowly added dropwise. The mixture is allowed to warm up to 22° C. and the precipitate is filtered off and washed thoroughly with diethyl ether and tetrahydrofuran. The filtrate is concentrated in vacuo.

Recrystallisation from ethyl acetate/petrol 40-60 (1/5) yielded the product 3 as colourless needles (9.70 g, 84%): $^1$H-NMR (300 MHz, CDCl$_3$) δ 7.07 (s, 2H), 4.77 (s, 4H), 2.39 (s, 6H).

4,7-Dimethyl-3H-isobenzofuran-1-one 4

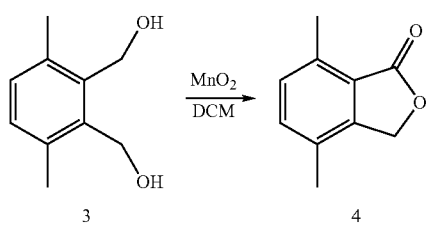

A 1 L 3-necked RBF is charged with 1,2-bis(hydroxymethyl)-3,6-dimethyl-benzene 3 (22.05 g, 0.133 mol), activated 85% manganese(IV) oxide (135.69 g, 1.327 mol), 4 Å molecular sieves (12.00 g) and anhydrous dichloromethane (500 mL), and placed under nitrogen. The reaction mixture is heated to reflux and stirred for 22 h. The reaction mixture is filtered through Kieselguhr and washed thoroughly with dichloromethane. The filtrate is concentrated in vacuo to yield the product 4 as a cream solid (19.79 g, 92%): $^1$H-NMR (300 MHz, CDCl$_3$) δ 7.31 (d, 1H, $^3$J=7.5 Hz), 7.18 (d, 1H, $^3$J=7.5 Hz), 5.18 (s, 2H), 2.65 (s, 3H), 2.29 (s, 3H); $^{13}$C-NMR (75 MHz, CDCl$_3$) δ 171.7, 145.8, 136.9, 134.5, 130.8, 129.3, 122.9, 68.3, 16.96, 16.91.

1-Methoxy-4,7-dimethyl-1,3-dihydro-isobenzofuran 5

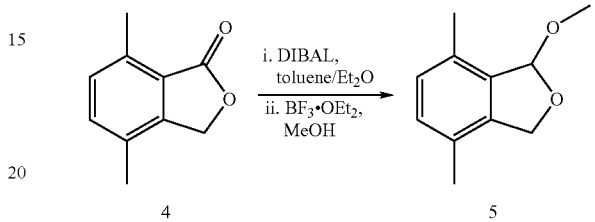

A 1.0M solution of diisobutylaluminium hydride (115 mL, 0.115 mol) in toluene is added dropwise over a period of 30 mins to a stirred solution of 4,7-dimethyl-3H-isobenzofuran-1-one 4 (18.66 g, 0.115 mol) in anhydrous toluene (250 mL) at −15° C. under nitrogen. Anhydrous diethyl ether (100 mL) is added and the reaction mixture is stirred 4 h at −50° C. The reaction mixture is removed from the cooling bath and diethyl ether (300 mL) is immediately added followed by saturated brine (200 mL). The organic layer is separated and the aqueous layer is re-extracted with diethyl ether (200 mL). The combined organics are dried over sodium sulfate and concentrated in vacuo to yield a cream solid. The solid is dissolved in anhydrous methanol (400 mL) and boron trifluoride diethyl etherate (2.3 mL, 0.018 mol) is added at 0° C. and the solution is stirred for 20 h at RT under nitrogen. The reaction mixture is poured into brine (200 mL) and extracted with petrol 40-60 (2×200 mL). The combined extracts are washed with water (3×100 mL), dried over sodium sulphate, and concentrated in vacuo to yield the product 5 as a yellow oil (17.14 g, 84%): $^1$H-NMR (300 MHz, CDCl$_3$) δ 7.03 (q, 2H, $^3$J=7.5 Hz, 4.5 Hz), 6.20 (s, 1H), 5.15 (d, 1H, $^3$J=13.5 Hz), 4.98 (d, 1H, $^3$J=13 Hz), 3.42 (s, 3H), 2.31 (s, 3H), 2.20 (s, 3H); $^{13}$C-NMR (75 MHz, CDCl$_3$) δ 138.7, 135.3, 130.8, 130.2, 129.1, 128.3, 107.7, 72.2, 54.0, 18.1, 17.5.

1,4,8,11-Tetramethyl-5,14,7,12-diepoxy-5,7,12,14-octahydropentacene-6,13-dione 7 via 4,7-Dimethyl-isobenzofuran 6

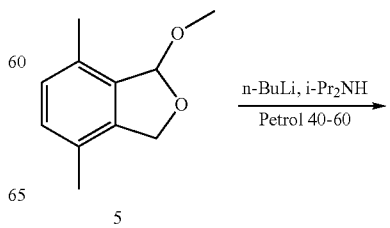

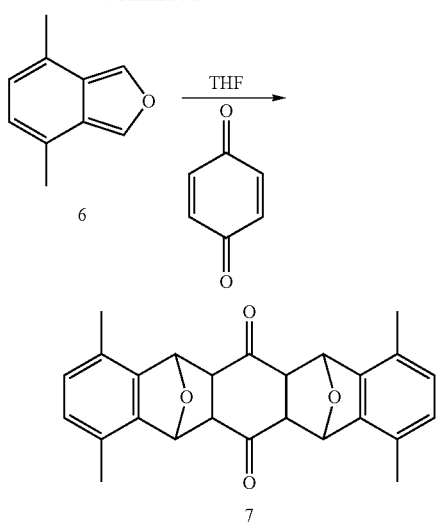

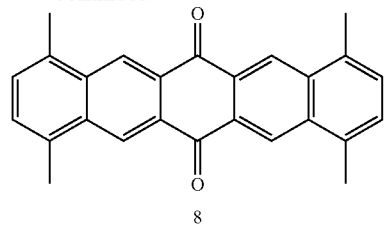

1,4,8,11-Tetramethyl-5,14,7,12-diepoxy-5,7,12,14-octahydropentacene-6,13-dione 7 (1.27 g, 3.17 mmol), sodium acetate (0.13 g, 1.53 mmol) and methanol (10 mL) are charged into a 20 mL microwave vial and heated in a microwave reactor (Emrys Creator, Personal Chemistry Ltd.) at 160° C. (5 mins). The precipitate that formed is filtered off, washed with cold methanol, and dried under vacuum to yield the product 8 as a brown crystalline solid (0.98 g, 85%): $^1$H-NMR (300 MHz, CDCl$_3$) δ9.13 (s, 4H), 7.43 (s, 4H), 2.85 (s, 12H); $^{13}$C-NMR not measurable due to low solubility.

A 1.6M n-butylithium solution in hexanes (120 mL, 0.191 mol) is added dropwise to a stirred solution of diisopropylamine (27 mL, 0.191 mol) in anhydrous petrol 40-60 (200 mL) at 0° C. under nitrogen. The lithium diisopropylamide solution is stirred at 0° C. for 30 mins and then added dropwise to a stirred solution of 1-methoxy-4,7-dimethyl-1,3-dihydro-isobenzofuran 5 (17.04 g, 0.096 mol) in anhydrous petrol 40-60 (500 mL) at 0° C. under nitrogen. The reaction mixture is allowed to warm to 22° C. and stirred for 3 h. Water (500 mL) is added to the reaction mixture and the organic layer is separated. The aqueous layer is re-extracted with petrol 40-60 (200 mL). The combined extracts are washed with water (2×200 mL) and dried over sodium sulfate. The solution of 4,7-dimethyl-isobenzofuran 6 in petroleum ether 40-60 (ca. 800 mL) is charged to a 2 L 3-necked RBF under nitrogen and a solution of p-benzoquinone in tetrahydrofuran (100 mL) is added dropwise at 22° C. The reaction mixture is stirred for 17 h. The solvents are removed in vacuo. The solids are dissolved in a small volume of tetrahydrofuran and a large excess of petrol 40-60 is added to precipitate the product. The crude product is filtered off, washed with petrol 40-60, and dried under vacuum to yield a brown solid. Recrystallisation from dichloromethane yielded the product 7 as white crystals (5.54 g, 29%): $^1$H-NMR (300 MHz, CDCl$_3$) δ6.90 (s, 4H), 5.59 (m, 4H), 2.47 (m, 4H), 2.22 (s, 12H); $^{13}$C-NMR (75 MHz, CDCl$_3$) δ 205.4, 141.2, 129.3, 127.8, 81.5, 51.0, 17.9.

1,4,8,11-Tetramethyl-6,13-pentacenequinone 8

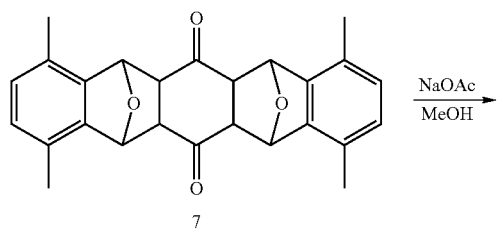

1,4,8,11-Tetramethyl-6,13-bis(triethylsilylethynyl) pentacene 9

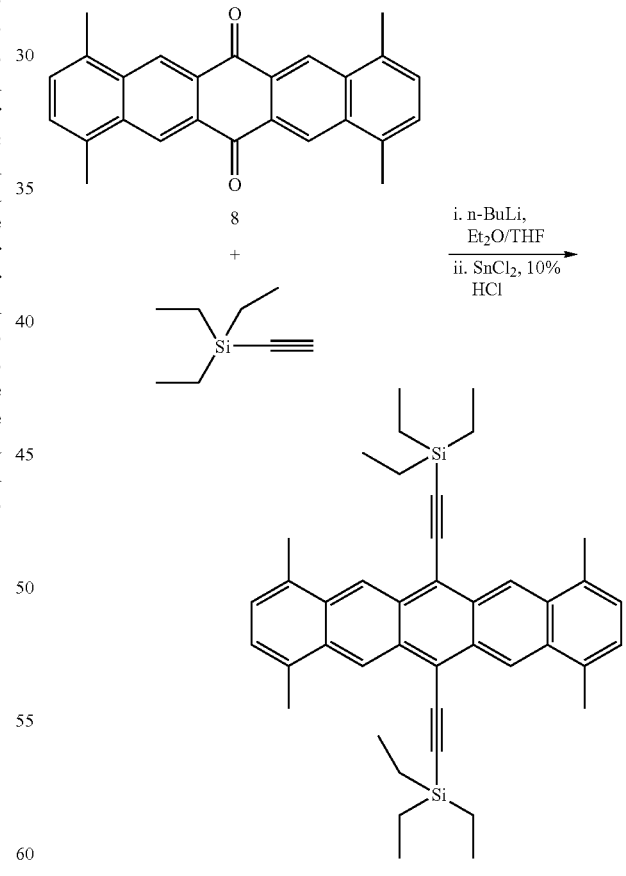

A 3-necked 500 mL RBF is charged with triethylsilylacetylene (6.1 mL, 34.11 mmol) and anhydrous diethyl ether (100 mL) under nitrogen. The solution is cooled to 0° C. and a solution of 2.5 M n-butyllithium in hexanes (12.4 mL, 31.01 mmol) is added dropwise. The reaction mixture is removed from the ice-bath and stirred for 1 h at 22° C. 1,4,8,11-Tetramethyl-6,13-pentacenequinone 8 (1.13 g, 3.10 mmol) is added and the reaction mixture is stirred at 22° C. for 2 h. Anhydrous tetrahydrofuran (100 mL) is added and the reaction mixture is stirred for a further 18 h. A saturated solution of stannous(II) chloride in 10% HCl solution (20 mL) is added and the solution is stirred under nitrogen for 30 mins. The reaction mixture is poured into water (300 mL) and extracted with dichloromethane (300 mL). The aqueous layer is re-extracted with dichloromethane (2×100 mL). The combined extracts are dried over sodium sulfate and concentrated in vacuo. The crude product is dissolved in a small volume of dichloromethane, acetone (100 mL) is added, and the mixture is stirred for 30 mins. The solid is filtered off, washed with cold acetone and methanol, and dried under vacuum to yield the product 9 as a dark blue solid (1.15 g, 61%): $^1$H-NMR (300 MHz, CDCl$_3$) δ9.40 (s, 4H), 7.16 (s, 4H), 2.82 (s, 12H), 1.30 (t, 18H, $^3$J=8 Hz), 0.94 (q, 12H, $^3$J=8 Hz); $^{13}$C-NMR (75 MHz, CDCl$_3$) δ 132.8, 132.4, 130.1, 125.9, 123.2, 118.2, 107.6, 104.1, 19.6, 8.0, 4.8.

Example 2

A top gate OFET device as exemplarily shown in FIG. 6 is prepared as described in WO 2005/055248 A2. Compound (9) of example 1 is dissolved with the binder material poly (alpha-methylsyrene) (1:1 ratio) at 4% total solids content in tetralin. The resulting solution is spin-coated upon masked Pt/Pd patterned source/drain electrodes on a PEN substrate. A solution of the dielectric material Lisicon™ D139 (commercially available from Merck KGaA, Darmstadt, Germany) is used as the gate insulator layer. A gold gate contact is provided onto the coated and dried gate insulator layer by evaporation through a shadow mask.

Figure 7:
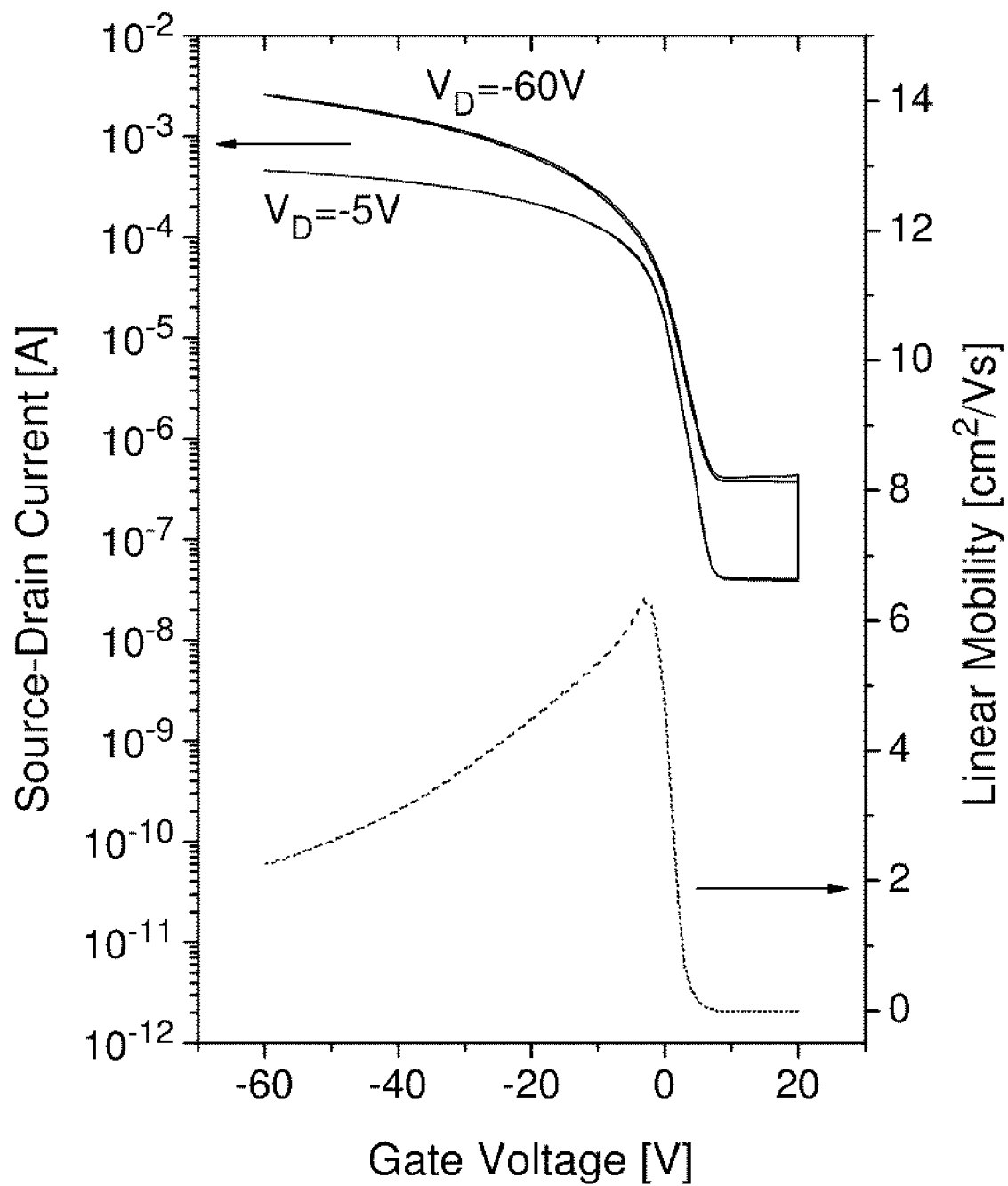
FIG. 7 shows the characteristics of an OFET device according to Example 2.

The device performance is measured as described in WO 03/052841 A1. FIG. 7 shows the transfer characteristics, mobility and on/off ratio of the OFET. The device shows high mobility and a high on/off ratio:
$\mu_{lin}$=6.3 cm$^2$/Vs (linear mobility)
$I_{on}/I_{off}$=7×10$^3$ (current on/off ratio)

The invention claimed is:

1. A process for preparing a 1,4,8,11-tetrasubstituted pentacene comprising the following steps:
   a1) reducing a 4,7-disubstituted isobenzofuran-1,3-dione (2) in the presence of a reducing agent to form the 4,7-disubstituted 3H-isobenzofuran-1-one (4),
   or
   a2) oxidizing a 1,2-bis(hydroxymethyl)-3,6-disubstituted benzene (3) in the presence of an oxidizing agent to form a 4,7-disubstituted 3H-isobenzofuran-1-one (4),
   or
   a3) oxidizing a 1,2-bis(hydroxymethyl)-3,6-disubstituted benzene (3) in the presence of an oxidizing agent to form a 4,7-disubstituted 1-hydroxy-1,3-dihydro-isobenzofuran (5a),
   and, in case of step a1) or step a2),
   b) reducing the product (4) of step a1) or a2) in the presence of a reducing agent to form a 4,7-disubstituted 1-hydroxy-1,3-dihydro-isobenzofuran (5a),
   and
   c) methylating the product (5a) of step a3) or b) to form a 4,7-disubstituted 1-methoxy-1,3-dihydro-isobenzofuran (5b),
   d) eliminating the product (5b) of step c) in the presence of a base to form a 4,7-disubstituted isobenzofuran (6),
   e) reacting the product (6) of step d) with p-benzoquinone by Diels-Alder cycloaddition to form a bis-cycloadduct (7),
   f) dehydrating the product (7) of step e) in the presence of a base to form a 1,4,8,11-tetrasubstituted 6,13-pentacenequinone (8), and
   g) alkynating the product (8) of step f) with a monosubstituted metal acetylide to form a 1,4,8,11-tetrasubstituted 6,13-bis(1-substituted ethynyl)pentacene (9).

2. The process according to claim 1, wherein the educt (2) of step a1) and the educt (3) of steps a2) and a3) are prepared by the following steps:
   x1) reacting 2,5-disubstituted furan with maleic anhydride by Diels-Alder cycloaddition to form a cycloadduct (1),
   x2) dehydrating the product (1) of step x1) in the presence of an acid to form a 4,7-disubstituted isobenzofuran-1,3-dione (2),
   and, in case of preparing (3), and
   x3) reducing the product (2) of step x2) in the presence of a hydride reagent to form 1,2-bis(hydroxymethyl)-3,6-disubstituted benzene (3).

3. The process according to claim 1, wherein the 1,4,8,11-tetrasubstituted pentacene is selected of formula I

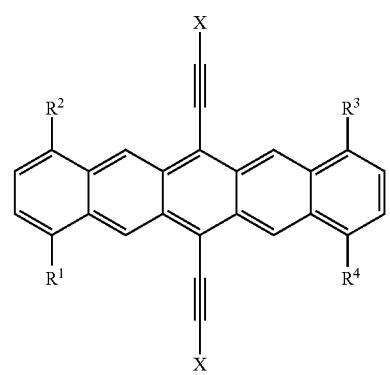

I wherein
X is SiR$^5$R$^6$R$^7$ or Ar,
R$^{1-7}$ are identical or different carbyl or hydrocarbyl groups,
Ar is in each occurrence independently of one another an optionally substituted aryl or heteroaryl group.

4. The process according to claim 3, wherein the 1,4,8,11-tetrasubstituted pentacene is selected from the following formulae:

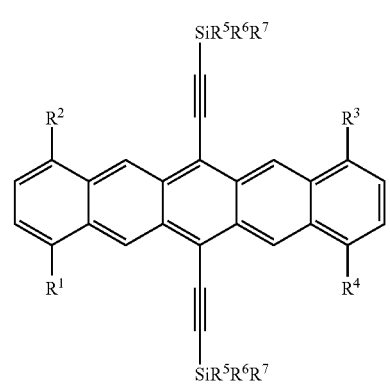

Ia

-continued

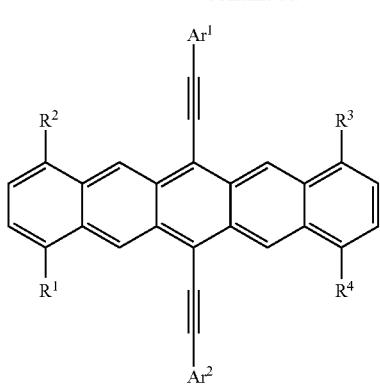

Ib wherein $R^{1-7}$ are identical or different carbyl or hydrocarbyl groups, and $Ar^1$ and $Ar^2$ are identical or different aromatic or heteroaromatic ring systems.

5. The process according to claim 4, wherein $Ar^1$ and $Ar^2$ are selected from 4-alkylphenyl or 2,4,6-trialkylphenyl.

6. The process according to claim 3, wherein $R^{1-4}$ are selected from $C_{1-12}$ alkyl, fluoroalkyl or alkoxy, F, Cl or cyano.

7. A compound obtained by the process according to claim 1, wherein the compound is of formula I:

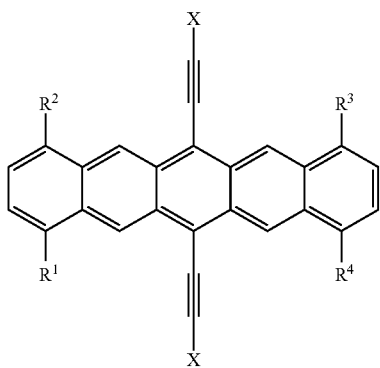

I wherein
X is Ar,
$R^{1-7}$ are identical or different carbyl or hydrocarbyl groups,
Ar is in each occurrence independently of one another an optionally substituted aryl or heteroaryl group.

8. Formulation comprising one or more compounds of claim 7 and one or more solvents.

9. Charge transport, semiconducting, electrically conducting, photocon-ducting or light emitting material or component comprising one or more formulations according to claim 8.

10. Optical, electrooptical, electronic, electroluminescent or photoluminescent component or device comprising one or more formulations-according to claim 8.

11. The formulation comprising one or more compounds of claim 7 and one or more organic binders, or precursors thereof, and optionally one or more solvents.

12. Charge transport, semiconducting, electrically conducting, photocon-ducting or light emitting material or component comprising one or more formulations according to claim 11.

13. Optical, electrooptical, electronic, electroluminescent or photoluminescent component or device comprising one or more formulations-according to claim 11.

14. Charge transport, semiconducting, electrically conducting, photocon-ducting or light emitting material or component comprising one or more compounds according to claim 7.

15. Optical, electrooptical, electronic, electroluminescent or photoluminescent component or device comprising one or more compounds according to claim 7.

16. Component or device according to claim 15, wherein it is selected from electrooptical displays, LCDs, optical films, retarders, compensators, polarisers, beam splitters, reflective films, alignment layers, colour filters, holographic elements, hot stamping foils, coloured images, decorative or security markings, LC pigments, adhesives, non-linear optic (NLO) devices, optical information storage devices, electronic devices, organic semiconductors, organic field effect transistors (OFET), integrated circuits (IC), thin film transistors (TFT), Radio Frequency Identification (RFID) tags, organic light emitting diodes (OLED), organic light emitting transistors (OLET), electroluminescent displays, organic photovoltaic (OPV) devices, organic solar cells (O-SC), organic laser diodes (O-laser), organic integrated circuits (O-IC), lighting devices, sensor devices, electrode materials, photoconductors, photodetectors, electrophotographic recording devices, capacitors, charge injection layers, Schottky diodes, planarising layers, antistatic films, conducting substrates, conducting patterns, photoconductors, electrophotographic applications, electrophotographic recording, organic memory devices, biosensors, or biochips.

* * * * *